(12) United States Patent
Tran et al.

(10) Patent No.: US 12,116,411 B2
(45) Date of Patent: Oct. 15, 2024

(54) ANTIBODIES BINDING TO HUMAN CD3 AT ACIDIC PH

(71) Applicant: Abzyme Therapeutics LLC, Pottstown, PA (US)

(72) Inventors: Hiep Tran, West Chester, PA (US);
Carla Campbell, Royersford, PA (US);
Byung Lee, Watertown, MA (US);
Fouad Moussa, Allentown, PA (US);
Andrew Phillips, Pottstown, PA (US);
Rajesh Singh, Malvern, PA (US);
Laura DeCristofano, Phoenixville, PA (US)

(73) Assignee: Abzyme Therapeutics LLC, Pottstown, PA (US)

( * ) Notice: Subject to any disclaimer, the term of this patent is extended or adjusted under 35 U.S.C. 154(b) by 0 days.

(21) Appl. No.: 17/517,258

(22) Filed: Nov. 2, 2021

(65) Prior Publication Data

US 2022/0135680 A1 May 5, 2022

Related U.S. Application Data

(60) Provisional application No. 63/109,005, filed on Nov. 3, 2020.

(51) Int. Cl.
| | | |
|---|---|---|
| *C07K 16/28* | (2006.01) | |
| *A61K 39/395* | (2006.01) | |
| *A61K 45/06* | (2006.01) | |
| *A61P 35/00* | (2006.01) | |

(52) U.S. Cl.
CPC ...... *C07K 16/2809* (2013.01); *A61K 39/3955* (2013.01); *A61K 45/06* (2013.01); *A61P 35/00* (2018.01); *C07K 2317/24* (2013.01); *C07K 2317/56* (2013.01); *C07K 2317/565* (2013.01); *C07K 2317/92* (2013.01)

(58) Field of Classification Search
CPC ............ C07K 16/2809; C07K 2317/24; C07K 2317/56; C07K 2317/565; C07K 2317/92; C07K 2317/30; C07K 2317/622; C07K 2317/75; A61K 39/3955; A61K 45/06; A61P 35/00
See application file for complete search history.

(56) References Cited

U.S. PATENT DOCUMENTS 5,595,756 A * 1/1997 Bally et al. .......... A61K 9/1272

FOREIGN PATENT DOCUMENTS

WO  WO-2016014974 A2 * 1/2016 ........... A61K 39/395
WO  WO-2019241216 A1 * 12/2019 ............. A61K 47/60

OTHER PUBLICATIONS

Heppner et al., Tumor heterogeneity: biological implications and therapeutic consequences, 1983, Cancer Metastasis Reviews 2: 5-23 (Year: 1983).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Greenspan et al. 1999 Defining epitopes: It's not as easy as it seems; Nature Biotechnology, 17:936-937 (Year: 1999).*
Bork. Powers and Pitfalls in Sequence Analysis: The 70% Hurdle. Genome Research, 2000, 10:398-400 (Year: 2000).*
Gera et al., (2012), Design of pH Sensitive Binding Proteins from the Hyperthermophilic Sso7d Scaffold. PLoS One 7(11): e48928 (Year: 2012).*
Pegu et al., Activation and lysis of human CD4 cells latently infected with HIV-1, (2015), Nat Commun 6, 8447, pp. 1-9 (Year: 2015).*
Wu et al., Multiple Signaling Roles of CD38ε and Its Application in CAR-T Cell Therapy, 2020, Cell 182:855-871 (Year: 2020).*
Sulea et al., Structure based engineering of pH-dependent antibody binding for selective targeting of solid-tumor microenvironment, 2020, mAbs, 12:1, 1682866 (15 pages) (Year: 2019).*
Schwab et al.; "Requirements for T Cell activation by OKT3 monoclonal antibody: role of modulation of T3 molecules and interleukin 1", J Immunol. Sep. 1985;135(3):1714-8 Abstract.
Gopalakrishnapillai et al.; "Immunotherapeutic Targeting of Mesothelin Positive Pediatric AML Using Bispecific T Cell Engaging Antibodies"; Cancers 2021, 13, 5964.
Vafa et al.; "Perspective: Designing T-Cell Engagers With Better Therapeutic Windows"; Frontiers in Oncology; Apr. 2020, vol. 10, Article 446.

* cited by examiner

*Primary Examiner* — Adam Weidner
*Assistant Examiner* — Danaya L Middleton
(74) *Attorney, Agent, or Firm* — MOSER TABOADA

(57) ABSTRACT

The invention relates to new anti-hCD3 antibodies that, in contrast to prior art anti-CD3 antibodies, bind specifically to human CD3 at acidic pH, but do not significantly bind to human CD3 at neutral or physiological pH, methods to produce these antibodies and therapeutic uses of these antibodies. These antibodies are able to activate T cells at acidic pH while having significantly reduced activity at neutral or physiological pH.

15 Claims, 10 Drawing Sheets

Specification includes a Sequence Listing.

OKT3 VH SEQ ID NO: 11

QVQLQQSGAELARPGASVKMSCKASGYTFTRYTMHWVKQRPGQGLEWIGYINPSRGYTNY
NQKFKDKATLTTDKSSSTAYMQLSSLTSEDSAVYYCARYYDDHYCLDYWGQGTTLTVSS

Humanized OKT3 VH SEQ ID NO: 12

QIQLVQSGAEVAKPGASVKVSCKASGYTFTRYTMHWVRQRPGQGLEWIGYINPSRGYTNY
NQKFKDRATLTTDKSTSTAYMELSSLTSEDTAVYYCARYYDDHYCLDYWGQGTTVTVSS

OKT3 VL SEQ ID NO: 14

QIVLTQSPAIMSASPGEKVTMTCSASSSVSYMNWYQQKSGTSPKRWIYDTSKLASGVPAHFR
GSGSGTSYSLTISGMEAEDAATYYCQQWSSNPFTFGSGTKLEIK

Humanized OKT3 VL SEQ ID NO:15

DIQLTQSPSSLSASVGDRVTITQRASSSVSYMNWYQQKSGTAPKRWIYDTSKVASGVPYRFS
GSGSGTSYTLTISSLQPEDAATYYCQQWSSNPLTFGGGTKVEIK

Figure 1

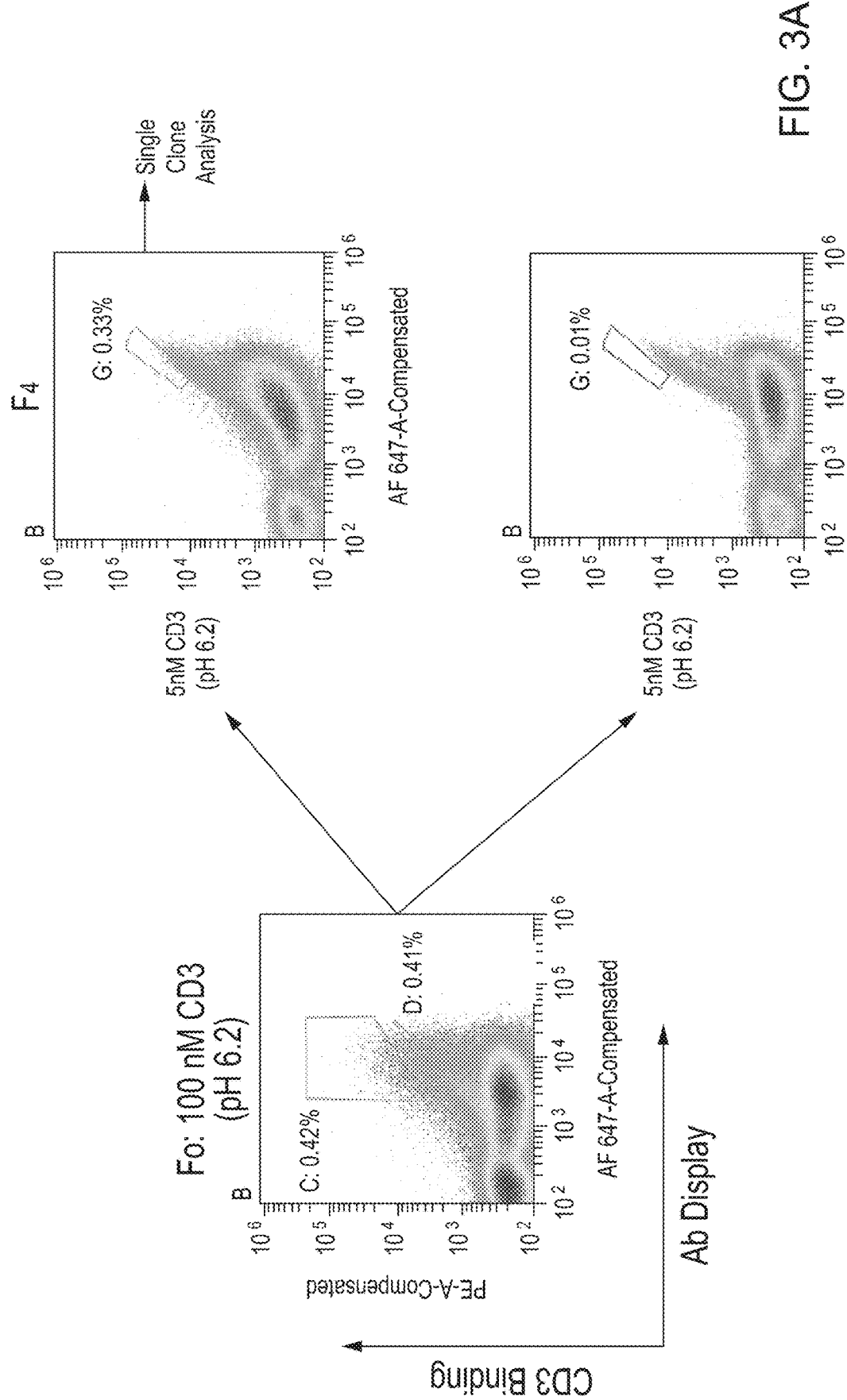

SEQUENCE LISTING

```
<160> NUMBER OF SEQ ID NOS: 34

<210> SEQ ID NO 1
<211> LENGTH: 5
<212> TYPE: PRT
<213> ORGANISM: Murine

<400> SEQUENCE: 1

Arg Tyr Thr Met His
1               5

<210> SEQ ID NO 2
<211> LENGTH: 18
<212> TYPE: PRT
<213> ORGANISM: Murine

<400> SEQUENCE: 2

Gly Tyr Ile Asn Pro Ser Arg Gly Tyr Thr Asn Tyr Asn Gln Lys Phe
1               5                   10                  15

Lys Asp

<210> SEQ ID NO 3
<211> LENGTH: 18
<212> TYPE: PRT
<213> ORGANISM: Artificial Sequence
<220> FEATURE:
<223> OTHER INFORMATION: Mutagenesis
```

```
<400> SEQUENCE: 3

Gly Tyr Ile Asn Pro Ser His Gly Tyr Thr Asn Tyr Asn Gln Lys Phe
1               5                   10                  15

Lys Asp

<210> SEQ ID NO 4
<211> LENGTH: 11
<212> TYPE: PRT
<213> ORGANISM: Murine

<400> SEQUENCE: 4

Arg Tyr Tyr Asp Asp His Tyr Cys Leu Asp Tyr
1               5                   10

<210> SEQ ID NO 5
<211> LENGTH: 10
<212> TYPE: PRT
<213> ORGANISM: Murine

<400> SEQUENCE: 5

Ser Ala Ser Ser Ser Val Ser Tyr Met Asn
1               5                   10

<210> SEQ ID NO 6
<211> LENGTH: 10
<212> TYPE: PRT
<213> ORGANISM: Murine

<400> SEQUENCE: 6

Arg Ala Ser Ser Ser Val Ser Tyr Met Asn
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Mutagenesis

<400> SEQUENCE: 7

Arg Ala Ser Ser Ser Val His Tyr Met Asn
1               5                   10

<210> SEQ ID NO 8
<211> LENGTH: 8
<212> TYPE: PRT
<213> ORGANISM: Murine

<400> SEQUENCE: 8

Tyr Asp Thr Ser Lys Leu Ala Ser
1               5

<210> SEQ ID NO 9
<211> LENGTH: 9
<212> TYPE: PRT
<213> ORGANISM: Murine

<400> SEQUENCE: 9

Gln Gln Trp Ser Ser Asn Pro Phe Thr
1               5

<210> SEQ ID NO 10
<211> LENGTH: 9
```

<212> TYPE: PRT
<213> ORGANISM: Murine

<400> SEQUENCE: 10

Gln Gln Trp Ser Ser Asn Pro Leu Thr
1               5

<210> SEQ ID NO 11
<211> LENGTH: 119
<212> TYPE: PRT
<213> ORGANISM: Murine

<400> SEQUENCE: 11

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 12
<211> LENGTH: 119
<212> TYPE: PRT
<213> ORGANISM: Murine

<400> SEQUENCE: 12

Gln Ile Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Ala Thr Leu Thr Thr Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 13
<211> LENGTH: 119
<212> TYPE: PRT
<213> ORGANISM: Artificial Sequence
<220> FEATURE:
<223> OTHER INFORMATION: Mutagenesis

<400> SEQUENCE: 13

Gln Ile Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Arg Pro Gly Gln Gly Leu Glu Trp Ile
        35                  40                  45

Gly Tyr Ile Asn Pro Ser His Gly Tyr Thr Asn Tyr Asn Gln Lys Phe
    50                  55                  60

Lys Asp Arg Ala Thr Leu Thr Thr Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 14
<211> LENGTH: 106
<212> TYPE: PRT
<213> ORGANISM: Murine

<400> SEQUENCE: 14

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys
            100                 105

<210> SEQ ID NO 15
<211> LENGTH: 106
<212> TYPE: PRT
<213> ORGANISM: Murine

<400> SEQUENCE: 15

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

Asn Trp Tyr Gln Gln Lys Ser Gly Thr Ala Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Thr Leu Thr Ile Ser Ser Leu Gln Pro Glu
65                  70                  75                  80

```
Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 16
<211> LENGTH: 106
<212> TYPE: PRT
<213> ORGANISM: Artificial Sequence
<220> FEATURE:
<223> OTHER INFORMATION: Mutagenesis

<400> SEQUENCE: 16

Asp Ile Gln Leu Thr Gln Pro Pro Ser Ser Leu Ser Ala Ser Val Gly
1               5                   10                  15

Asp Arg Val Thr Ile Thr Cys Arg Ala Ser Ser Ser Val His Tyr Met
            20                  25                  30

Asn Trp Tyr Gln Gln Lys Ser Gly Thr Ala Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Thr Leu Thr Ile Ser Ser Leu Gln Pro Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 17
<211> LENGTH: 106
<212> TYPE: PRT
<213> ORGANISM: Artificial Sequence
<220> FEATURE:
<223> OTHER INFORMATION: Mutagenesis

<400> SEQUENCE: 17

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val His Tyr Met
            20                  25                  30

Asn Trp Tyr Gln Gln Lys Ser Gly Thr Ala Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Thr Leu Thr Ile Ser Ser Leu Gln Pro Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 18
<211> LENGTH: 244
<212> TYPE: PRT
<213> ORGANISM: Murine

<400> SEQUENCE: 18

Gln Val Gln Leu Gln Gln Ser Gly Ala Glu Leu Ala Arg Pro Gly Ala
1               5                   10                  15
```

```
Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Gln Ile Val Leu Thr Gln Ser
        130                 135                 140

Pro Ala Ile Met Ser Ala Ser Pro Gly Glu Lys Val Thr Met Thr Cys
145                 150                 155                 160

Ser Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Leu Ala Ser
            180                 185                 190

Gly Val Pro Ala His Phe Arg Gly Ser Gly Ser Gly Thr Ser Tyr Ser
            195                 200                 205

Leu Thr Ile Ser Gly Met Glu Ala Glu Asp Ala Ala Thr Tyr Tyr Cys
        210                 215                 220

Gln Gln Trp Ser Ser Asn Pro Phe Thr Phe Gly Ser Gly Thr Lys Leu
225                 230                 235                 240

Glu Ile Lys Arg

<210> SEQ ID NO 19
<211> LENGTH: 244
<212> TYPE: PRT
<213> ORGANISM: Murine

<400> SEQUENCE: 19

Gln Ile Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Arg Ala Thr Leu Thr Thr Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140
```

```
Pro Ser Ser Leu Ser Ala Ser Val Gly Asp Arg Val Thr Ile Thr Cys
145                 150                 155                 160

Arg Ala Ser Ser Val Ser Tyr Met Asn Trp Tyr Gln Gln Lys Ser
            165                 170                 175

Gly Thr Ala Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Thr
        195                 200                 205

Leu Thr Ile Ser Ser Leu Gln Pro Glu Asp Ala Ala Thr Tyr Tyr Cys
        210                 215                 220

Gln Gln Trp Ser Ser Asn Pro Leu Thr Phe Gly Gly Gly Thr Lys Val
225                 230                 235                 240

Glu Ile Lys Arg

<210> SEQ ID NO 20
<211> LENGTH: 244
<212> TYPE: PRT
<213> ORGANISM: Artificial Sequence
<220> FEATURE:
<223> OTHER INFORMATION: Mutagenesis

<400> SEQUENCE: 20

Gln Ile Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Ala Thr Leu Thr Thr Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Val Glu Gly Gly Ser Gly Gly Ser Gly
        115                 120                 125

Gly Ser Gly Gly Ser Gly Val Asp Asp Ile Gln Leu Thr Gln Pro
130                 135                 140

Pro Ser Ser Leu Ser Ala Ser Val Gly Asp Arg Val Thr Ile Thr Cys
145                 150                 155                 160

Arg Ala Ser Ser Val His Tyr Met Asn Trp Tyr Gln Gln Lys Ser
            165                 170                 175

Gly Thr Ala Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Thr
        195                 200                 205

Leu Thr Ile Ser Ser Leu Gln Pro Glu Asp Ala Ala Thr Tyr Tyr Cys
        210                 215                 220

Gln Gln Trp Ser Ser Asn Pro Leu Thr Phe Gly Gly Gly Thr Lys Val
225                 230                 235                 240

Glu Ile Lys Arg

<210> SEQ ID NO 21
```

```
<211> LENGTH: 244
<212> TYPE: PRT
<213> ORGANISM: Artificial Sequence
<220> FEATURE:
<223> OTHER INFORMATION: Mutagenesis

<400> SEQUENCE: 21

Gln Ile Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Arg Pro Gly Gln Gly Leu Glu Trp Ile
        35                  40                  45

Gly Tyr Ile Asn Pro Ser His Gly Tyr Thr Asn Tyr Asn Gln Lys Phe
    50                  55                  60

Lys Asp Arg Ala Thr Leu Thr Thr Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Val Glu Gly Gly Ser Gly Gly Ser Gly
        115                 120                 125

Gly Ser Gly Gly Ser Gly Gly Val Asp Ile Gln Leu Thr Gln Ser
    130                 135                 140

Pro Ser Ser Leu Ser Ala Ser Val Gly Asp Arg Val Thr Ile Thr Cys
145                 150                 155                 160

Arg Ala Ser Ser Ser Val Ser Tyr Met Asn Trp Tyr Gln Gln Lys Ser
                165                 170                 175

Gly Thr Ala Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Thr
        195                 200                 205

Leu Thr Ile Ser Ser Leu Gln Pro Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Arg

<210> SEQ ID NO 22
<211> LENGTH: 244
<212> TYPE: PRT
<213> ORGANISM: Artificial Sequence
<220> FEATURE:
<223> OTHER INFORMATION: Mutagenesis

<400> SEQUENCE: 22

Gln Ile Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Ala Thr Leu Thr Thr Asp Lys Ser Thr Ser Thr Ala Tyr
65                  70                  75                  80
```

-continued

```
Met Glu Leu Ser Ser Leu Thr Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ser Ser Leu Ser Ala Ser Val Gly Asp Arg Val Thr Ile Thr Cys
145                 150                 155                 160

Arg Ala Ser Ser Ser Val His Tyr Met Asn Trp Tyr Gln Gln Lys Ser
                165                 170                 175

Gly Thr Ala Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Thr
        195                 200                 205

Leu Thr Ile Ser Ser Leu Gln Pro Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Arg

<210> SEQ ID NO 23
<211> LENGTH: 122
<212> TYPE: PRT
<213> ORGANISM: Murine

<400> SEQUENCE: 23

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Met
        35                  40                  45

Gly Leu Ile Asn Pro Tyr Lys Gly Val Ser Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Thr Leu Thr Val Phe Ser
        115                 120

<210> SEQ ID NO 24
<211> LENGTH: 107
<212> TYPE: PRT
<213> ORGANISM: Murine

<400> SEQUENCE: 24

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30
```

```
Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Lys Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                85                  90                  95

Thr Phe Ala Gly Gly Thr Lys Leu Glu Ile Lys
            100                 105
```

<210> SEQ ID NO 25
<211> LENGTH: 247
<212> TYPE: PRT
<213> ORGANISM: Artificial Sequence
<220> FEATURE:
<223> OTHER INFORMATION: Fusion Protein

<400> SEQUENCE: 25

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Ser Lys Asn Thr
 65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gln Thr Val Val Thr Gln Glu Pro Ser
    130                 135                 140

Leu Thr Val Ser Pro Gly Gly Thr Val Thr Leu Thr Cys Gly Ser Ser
145                 150                 155                 160

Thr Gly Ala Val Thr Ser Gly Tyr Tyr Pro Asn Trp Val Gln Gln Lys
                165                 170                 175

Pro Gly Gln Ala Pro Arg Gly Leu Ile Gly Gly Thr Lys Phe Leu Ala
            180                 185                 190

Pro Gly Thr Pro Ala Arg Phe Ser Gly Ser Leu Leu Gly Gly Lys Ala
        195                 200                 205

Ala Leu Thr Leu Ser Gly Val Gln Pro Glu Asp Glu Ala Glu Tyr Tyr
    210                 215                 220

Cys Ala Leu Trp Tyr Ser Asn Arg Trp Val Phe Gly Gly Gly Thr Lys
225                 230                 235                 240

Leu Thr Val Leu Gly Gln Pro
                245
```

<210> SEQ ID NO 26
<211> LENGTH: 10
<212> TYPE: PRT
<213> ORGANISM: Artificial Sequence
<220> FEATURE:

```
<223> OTHER INFORMATION: Mutagenesis

<400> SEQUENCE: 26

Ser Ala Ser Ser Ser Val His Tyr Met Asn
1               5                   10

<210> SEQ ID NO 27
<211> LENGTH: 5
<212> TYPE: PRT
<213> ORGANISM: Mouse

<400> SEQUENCE: 27

Gly Tyr Thr Met Asn
1               5

<210> SEQ ID NO 28
<211> LENGTH: 18
<212> TYPE: PRT
<213> ORGANISM: Artificial Sequence
<220> FEATURE:
<223> OTHER INFORMATION: Mutagenesis

<400> SEQUENCE: 28

Gly Leu Ile Asn Pro Tyr His Gly Val Ser Thr Tyr Asn Gln Lys Phe
1               5                   10                  15

Lys Asp

<210> SEQ ID NO 29
<211> LENGTH: 14
<212> TYPE: PRT
<213> ORGANISM: Mouse

<400> SEQUENCE: 29

Arg Ser Gly Tyr Tyr Gly Asp Ser Asp Trp Tyr Phe Asp Val
1               5                   10

<210> SEQ ID NO 30
<211> LENGTH: 10
<212> TYPE: PRT
<213> ORGANISM: Mouse

<400> SEQUENCE: 30

Ala Ser Gln Asp Ile His Asn Tyr Leu Asn
1               5                   10

<210> SEQ ID NO 31
<211> LENGTH: 9
<212> TYPE: PRT
<213> ORGANISM: Mouse

<400> SEQUENCE: 31

Ile Tyr Tyr Thr Ser Arg Leu His Ser
1               5

<210> SEQ ID NO 32
<211> LENGTH: 9
<212> TYPE: PRT
<213> ORGANISM: Mouse

<400> SEQUENCE: 32

Gln Gln Gly Asn Thr Leu Pro Trp Thr
1               5

<210> SEQ ID NO 33
```

-continued

```
<211> LENGTH: 18
<212> TYPE: PRT
<213> ORGANISM: Mouse

<400> SEQUENCE: 33

Gly Leu Ile Asn Pro Tyr Lys Gly Val Ser Thr Tyr Asn Gln Lys Phe
1               5                   10                  15

Lys Asp

<210> SEQ ID NO 34
<211> LENGTH: 10
<212> TYPE: PRT
<213> ORGANISM: Mouse

<400> SEQUENCE: 34

Ala Ser Gln Asp Ile Arg Asn Tyr Leu Asn
1               5                   10
```

ANTIBODIES BINDING TO HUMAN CD3 AT ACIDIC PH

RELATED APPLICATIONS

This application claims the priority of U.S. Provisional Application No. 63/109,005, filed Nov. 3, 2020, the contents of which are incorporated herein by reference in their entirety.

SEQUENCE LISTING STATEMENT

Filed herewith is a Sequence Listing (name: ABZ005SequenceListing.txt, created: Nov. 2, 2021; sized: 24,294 bytes). The content of that Sequence Listing is incorporated herein by reference in its entirety.

FIELD OF THE INVENTION

The present invention relates to a method of screening anti-CD3 antibody variants and isolated anti-CD3 antibody variants which exhibit acidic pH-selective antigen binding. The invention is preferably directed to the anti-CD3 OKT3 antibody or biologically active variants and fragments thereof, wherein the original OKT3 antibody or variant or fragment thereof is engineered by modifications to the amino acid sequence within the variable regions. Specifically, the invention relates to the OKT3 antibody or biologically active variants or fragments thereof, wherein the CDR domains are modified by replacing one or more amino acid residues by histidine residues. The resulting modified anti-CD3 antibodies elicit improved pharmacokinetic properties with binding specifically to human CD3 at acidic pH, but do not significantly bind to human CD3 at neutral or physiological pH, thus selectively targeting the solid-tumor microenvironment.

INTRODUCTION

The following discussion of the background of the invention is merely provided to aid the reader in understanding the invention and is not admitted to describe or constitute prior art to the present invention.

T lymphocytes play a central role in the adaptive immune response to antigen. Naive T cells require two signals for their full activation (BRETSCHER 1999). The first signal is antigen-specific and is provided by interaction of the T-cell receptor (TCR) with MHC/peptide complex on an antigen-presenting cell (APC). The second signal is a co-stimulatory signal provided by the interactions between receptors on the T cell and their ligands on the APC. Engagement of both TCR/MHC and co-stimulatory interactions leads to T-cell activation via a number of intracellular pathways, including calcium calcineurin and RAS mitogen-activated protein kinase, and subsequent activation of transcription factors for a number of effector compounds, including cytokines such as IL-2.

T lymphocytes also can be activated by antibody T cell engagers. T cell engager antibodies have at least two arms, one arm binds to a T cell, another arm binds to a cancer cell. Thus, the cell-linking antibodies direct a host's immune system, more specifically the T cells' cytotoxic activity, against cancer cells. T cell engaging antibodies bound to target cells are known to trigger the cytotoxic activity of T-lymphocytes by crosslinking to CD3, irrespective of T-cell receptor specificity, major histocompatibility (MHC) restriction, or MHC down regulation on tumor cells (WU and CHEUNG 2018). Because the activation of T cells by engaging antibodies relies on neither high copy numbers of tumor surface antigen nor its intracellular trafficking, T-cell engaging antibodies may provide enhanced efficacy for cancer cells that express low levels of target antigen. In addition, due to multiple cytotoxic mechanisms, T cells engaged by cell-linking antibodies can potently target chemotherapy-resistant cancer cells and quiescent cancer stem cells (WU and CHEUNG 2018).

Unlike standard antibodies that have specificity for a single antigen, bispecific and multi-specific antibodies have multiple antigen specificity, allowing them to bind to two or more unique antigens at once and thereby facilitate cell-to-cell interactions. Multi-specific antibodies capable of cell-linking can retarget immune effector cells to cancer cells for achieving anti-tumor activity. In effector cell retargeting, cells such as natural killer (NK) cells, macrophages, and cytotoxic T lymphocytes are brought into contact with target tumor cells through one of their activating receptors to allow cytotoxic responses to be triggered. Although retargeting NK cells or macrophages has definite benefits, T cell retargeting may have the greatest potential as anti-neoplastic therapy. The extensive expansion these cells undergo upon activation and their ability to activate host immunity give T cells particular therapeutic power. Furthermore, by directing T cells to tumors, these potent effectors can target tumor cells specifically with a precision that standard chemotherapy and radiation cannot (HUEHLS et al. 2015).

While Blinatumomab (Amgen) and other T cell engagers have been successful in clinical trials for hematological cancers, no clinical successes using bi-specific T cell engager technology (BiTE) in solid tumors have been reported to date (BAEUERLE and REINHARDT 2009; KOBOLD et al. 2018). For BiTE, dose-limiting toxicity and short half-life can prohibit use in solid tumors. Sufficient dosing to reach poorly perfused tumors without causing serious adverse events (AEs) is challenging. Another problem with non-lymphoid tumors is that tumor-associated antigens (TAA) are often not exclusively expressed on cancer cells, raising the issue of on-target but off-tumor toxicities which can be dose and efficacy limiting. While short serum half-life can be addressed by the fusion of BiTE to Fc, the on-target off-tumor adverse events remain as non-tumor tissues also express TAA (KOBOLD et al. 2018). Overcoming on-target off-tumor T cell activation would allow both dose escalation and reduction of side effects.

Due to poor vascular perfusion, regional hypoxia, and fermentative glycolysis (KATO et al. 2013), the extracellular pH in most solid tumors is in the 6.0-6.8 range (GERWECK and SEETHARAMAN 1996; HARGUINDEY and RESHKIN 2017; ZHANG et al. 2010). Recently, marking of acidic regions with pH below 6.5 overlapped with the highly proliferative, invasive regions at the tumor-stroma interface (ESTRELLA et al. 2013; ROHANI et al. 2019). However, non-cancerous cells maintain their extracellular pH at physiological levels (7.3-7.4). Thus, a TAA-specific antibody with high binding affinity at acidic pH (pH 6.0-pH 6.8), but with none or reduced binding affinity at normal pH will significantly minimalize the on-target off-tumor toxicity.

One approach is to develop antibodies that exhibit pH-sensitive antigen binding. It has been shown that rational or combinatorial incorporation of histidines in the binding interfaces of antibodies and other proteins (SARKAR et al. 2002; CHAPARRO-RIGGERS et al. 2012; ITO et al. 1992; IGAWA et al. 2010; IGAWA et al. 2013; MURTAUGH et al. 2011; GERA et al. 2012; SULEA et al. 2020) can be commonly used to engineer pH-dependent binding. The basis for the pH-sensitive binding arises from the histidine's sensitivity to be protonated as a result of lowered pH-values in the microenvironment. In more detail, the histidines need to undergo a pKa-change upon binding in order to get protonated in a physiological pH-range (MURTAUGH et al. 2011). Protonation of histidine side chains in binding-interfaces can alter electrostatic interactions or may induce conformational changes that lead to pH-dependent differences in binding affinity (GERA et al. 2012). Balanced electrostatic and non-electrostatic components of the binding equilibrium determine the sensitivity of binding (MURTAUGH et al. 2011).

Several strategies have been published that aim for the engineering of pH-switches in proteins. Histidine (His) scanning, in which every single amino acid residue (e.g. within the CDR regions) is individually mutated to His, allows the characterization of single His substitution variants and identification of effective mutations. Creation of new variants by combining these substitutions can result in enhanced pH-dependent binding (MURTAUGH et al. 2011; CHAPARRO-RIGGERS et al. 2012; IGAWA et al. 2010; SULEA et al. 2020). Identification of residues that may contribute to pH-sensitivity upon replacement with histidinesy structure-based modeling can help to minimize effort & time that is needed during the histidine scanning approach. Crystal structures are required in order to have a precise idea of residues that are critical for binding and the rational design of pH-switches (SARKAR et al. 2002). Combinatorial histidine scanning library approaches require in vitro screening technologies to isolate pH-sensitive variants from a large molecule library. Murtaugh and colleagues designed a llama VHH antibody library by using oligonucleotide-directed mutagenesis thereby allowing every residue within the binding interface to sample both histidine residues and wild-type residues of the parental VHH antibody. Following screening of a M13-phage display library (diversity .about.10.sup.12) isolated variants showed KDs between 35-91 nM at pH 7.4 and about a 10.sup.4 fold decrease in binding affinity at pH 5.4 (MURTAUGH et al. 2011). Schroter and colleagues incorporated pH-sensitive antigen binding functions into antibody variable domains using combinatorial histidine scanning libraries and yeast surface display, and successfully isolated antibodies with high affinity binding at pH 7.4 in the sub-nanomolar range, while with significantly reduced binding at pH 6.0 (KD increased 230- to 780-fold) (SCHROTER et al. 2015).

Since the tumor microenvironment has acidic pH in the 6.0-6.8 range, while non-cancerous cells maintain the extracellular pH at physiological levels (7.3-7.4), antibodies that have significant binding at acidic pH, but do not significantly bind at neutral or physiological pH will have tumor selectivity. Accordingly, there is a general need to make available antibodies which are more effective in the tumor microenvironment with acidic pH. In contrast to previous antibodies with biased binding at neutral pH (MURTAUGH et al. 2011; SCHROTER et al. 2015) this invention relates to developing antibodies, specifically anti-human CD3 antibodies, that bind preferably at acidic pH for the purposes of tumor selectivity.

SUMMARY

Such anti-CD3-epsilon antibodies, methods for manufacturing the same, and methods of using the same, according to embodiments of the disclosure, substantially as shown in and/or described in connection with at least one of the figures, are disclosed. Various advantages, aspects, and novel features of the present disclosure will be more fully understood from the following description and drawings. The foregoing summary is not intended, and should not be contemplated, to describe each embodiment or every implementation of the present disclosure. Other and further embodiments of the present disclosure are described below. Furthermore, changes and modifications can be made to embodiments described herein without departing from the spirit and scope of the present disclosure and without demising the attendant advantages.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

FIG. 1. Amino acid sequences of variable regions of OKT3 antibody (DrugBank Accession Number DB00075) and its humanized version (Genebank Accession Number ALJ79286, (PEGU et al. 2015)). CDR regions are boxed. Amino acid residues that are interacting with CD3 epsilon are underlined. The sequences shown in the FIG. 1 are, sequentially, SEQ ID NO:11, SEQ ID NO:12, SEQ ID NO:14 and SEQ ID NO:15.

FIG. 3A. FACS sorting to isolate antibody clones binding to the target at acidic conditions.

Figure 2:
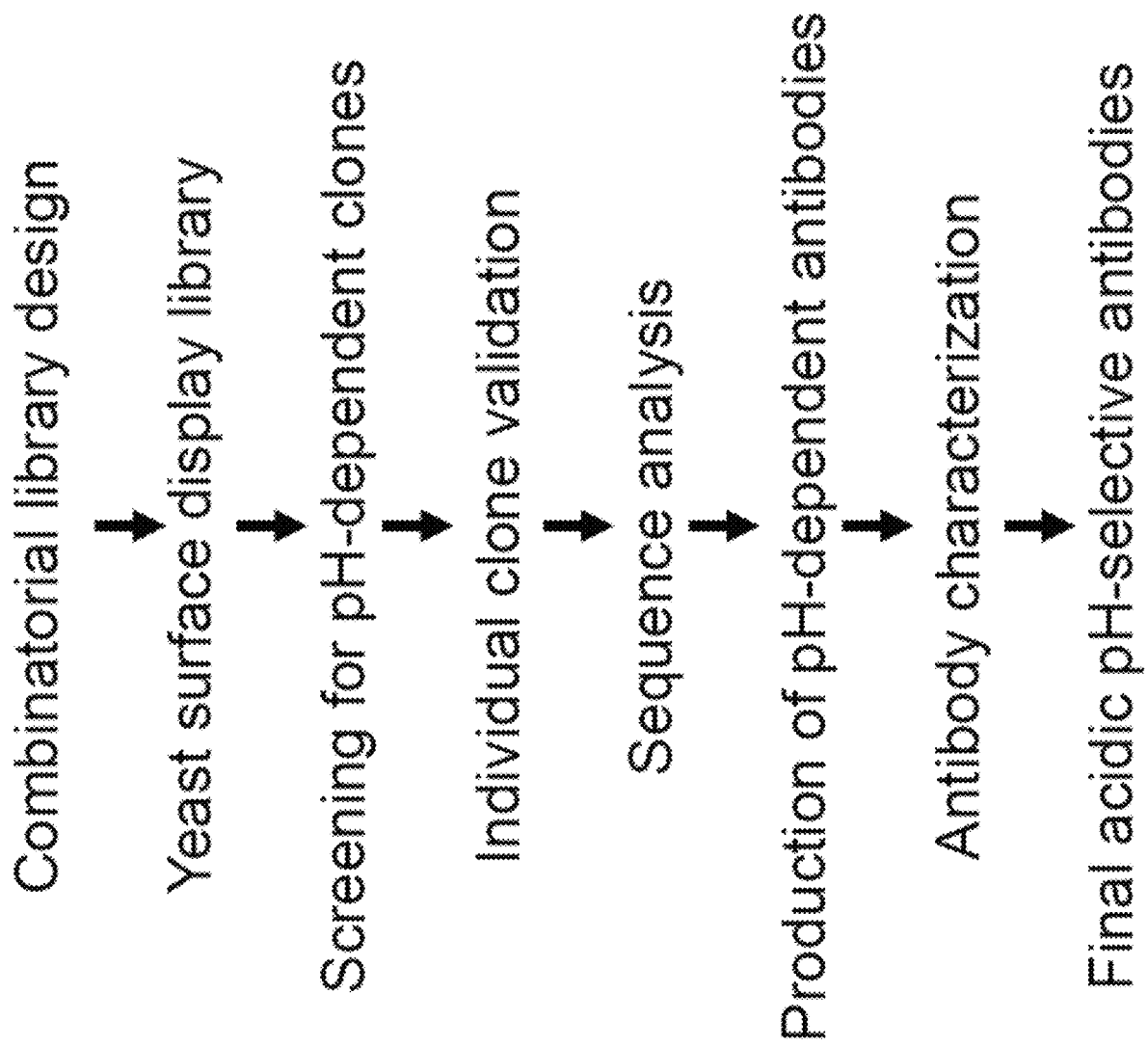
FIG. 2. Steps for isolation of pH-dependent antibodies.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

In the first aspect, the invention provides a method to generate pH-sensitive mutated forms of the anti-CD3 antibody OKT3, or other anti-CD3-epsilon antibodies, wherein the mutation consists of one or more amino acid substitutions of residues of the original, non-mutated antibody OKT3 by histidine residues in the complementary determining regions (CDRs) of the heavy and/or light chain variable domains of the antibody. The introduction of histidine residues at defined positions in some of the CDRs of OKT3 renders the original antibody much more pH-sensitive or pH-dependent compared to the non-mutated antibody. As a result of the histidine-substitution in the CDRs, the histidine-mutated antibody undergoes a significant loss of binding affinity at neutral or physiological pH (up to factor 5 and more of KD increase), while retaining binding affinity at acidic pH, resulting in the possibility for selective targeting of solid-tumor microenvironments and dose-escalation in cancer treatment.

The successful introduction of histidine residues according to the invention by replacement of original amino acid residues in the CDRs of OKT3 or biologically active variants and fragments thereof, resulting in the desired degree of pH-sensitivity and binding affinity could not be an anticipated result to one skilled the current state of the art.

The present invention provides a method for isolating pH-sensitive antibodies comprised of (i) design and synthesis of histidine-scanning combinatorial libraries, (ii) a surface display system, (iii) expressing one or more polynucleotides encoding an antibody variant that is fused to a cell surface anchor (for example, without limitation, S. cerevisiae AGA2); (iv) isolating host cells expressing antibody variants reactive to a target at acidic pH but not at neutral or physiological pH by either biological panning or FACS. Structure-based analysis (KJER-NIELSEN et al. 2004) has identified amino acid residues in OKT3 CDRs that interact with human CD3 receptors. There are five amino acid residues in the light chain and nine amino acid residues in the heavy chain that interact with CD3 epsilon (FIG. 1). All interacting amino acid residues excepting one are located in the CDR regions.

In the second aspect, the invention provides an anti-CD3 antibody or an antigen binding fragment thereof with pH dependent antigen binding comprising the light and heavy chain variable regions ("LCVRs" and "HCVRs") of therapeutic antibody OKT3 or a variant thereof with significantly reduced biological activity at neutral or physiological pH, while retaining the binding activity at acidic pH, wherein at least one of the CDR domains of the light and/or the heavy chain variable regions is mutated by replacement of one or more amino acids within said CDR domains by a histidine residue. A mutated anti-CD3-epsilon antibody variant elicits a pH dependent antigen binding with an antigen dissociation rate (Kos) ratio pH7/pH6 measured by Biolayer Interferometry (Octet interferometer), or other comparable methods, which is at least 5, 10, 15 or 100 fold higher compared to the respective $K_{dis}$ rate ratio of a non-mutated antibody.

Preferably the antibody or antigen binding fragment of the present invention is a humanized antibody comprising two heavy chains and two light chains.

In a further embodiment, the invention provides a respective mutated anti-CD3-epsilon antibody, wherein the mutated antibody or antigen binding fragment thereof has a similar biological activity of antigen binding affinity at acidic pH 6.0-6.8 as non-mutated anti-CD3-epsilon antibody has at neutral pH.

The invention provides anti-CD3 antibodies derived from OKT3, wherein one or more original amino acid residues within the CDRs of parental OKT3 were replaced by histidine residues.

Thus, the invention provides mutated anti-CD3-epsilon antibody or antigen binding fragment thereof comprising a CDR-H1, a CDR-H2 and a CDR-H3 heavy chain sequence selected from the groups consisting of:

TABLE 1

CDR-H regions of OKT3 and isolated OKT3 heavy chain with histidine replacement:

| Heavy chain | CDR-H1 | CDR-H2 | CDR-H3 |
|---|---|---|---|
| OKT3 | SEQ ID NO: 1 RYTMH | SEQ ID NO: 2 GYINPSRGYTNYN QKFKD | SEQ ID NO: 4 RYYDDHYCLDY |
| Abz287a (humanized OKT3 ScFV) | SEQ ID NO: 1 RYTMH | SEQ ID NO: 2 GYINPSRGYTNYN QKFKD | SEQ ID NO: 4 RYYDDHYCLDY |
| Abz494 | SEQ ID NO: 1 RYTMH | SEQ ID NO: 2 GYINPSRGYTNYN QKFKD | SEQ ID NO: 4 RYYDDHYCLDY |
| Abz495 | SEQ ID NO: 1 RYTMH | SEQ ID NO: 3 GYINPS<u>H</u>GYTNYN QKFKD | SEQ ID NO: 4 RYYDDHYCLDY |
| Abz497 | SEQ ID NO: 1 RYTMH | SEQ ID NO: 2 GYINPSRGYTNYN QKFKD | SEQ ID NO: 4 RYYDDHYCLDY |

Note: OKT3 is murine anti-CD3 antibody (DrugBank Accession Number DB00075); Abz287a is humanized version of OKT3, Abz494 to Abz498 are pH-dependent antibodies isolated in this invention. The sequence of Abz287a is found in GenBank Accession No. ALJ79286 and described (PEGU et al. 2015). Changes notes relative to Abz287a.

The invention further provides mutated anti-CD3-epsilon antibody or antigen binding fragment thereof comprising a CDR-L1, a CDR-L2 and a CDR-L3 light chain sequence selected from the groups consisting of:

TABLE 2

CDR-L regions of OKT and isolated OKT3 light chain with histidine replacement:

| Light chain | CDR-L1 | CDR-L2 | CDR-L3 |
|---|---|---|---|
| OKT3 | SEQ ID NO: 5 SASSSVSYMN | SEQ ID NO: 8 YDTSKLAS | SEQ ID NO: 9 QQWSSNPFT |
| Abz287a | SEQ ID NO: 6 RASSSVSYMN | SEQ ID NO: 8 YDTSKLAS | SEQ ID NO: 10 QQWSSNPLT |
| Abz494 | SEQ ID NO: 7 RASSSV<u>H</u>YMN | SEQ ID NO: 8 YDTSKLAS | SEQ ID NO: 10 QQWSSNPLT |
| Abz495 | SEQ ID NO: 5 SASSSVSYMN | SEQ ID NO: 8 YDTSKLAS | SEQ ID NO: 10 QQWSSNPLT |
| Abz497 | SEQ ID NO: 7 RASSSV<u>H</u>YMN | SEQ ID NO: 8 YDTSKLAS | SEQ ID NO: 10 QQWSSNPLT |

It was found by the inventors that preferable versions of histidine-mutated anti-CD3-epsilon antibody comprise one of the following heavy chain variable regions:

TABLE 3

Heavy chains of OKT3 and isolated acidic pH-selective OKT3 variants:

| OKT3 | SEQ ID | QVQLQQSGAELARPGASVKMSCKASGYTFTRYTMHWVK QRPGQGLEWIGYINPSRGYTNYNQKFKDKATLTTDKSS |
|---|---|---|

TABLE 3-continued

Heavy chains of OKT3 and isolated acidic
pH-selective OKT3 variants:

|  |  |  |
|---|---|---|
|  | NO:<br>11 | STAYMQLSSLTSEDSAVYYCARYYDDHYCLDYWGQGTT<br>LTVSS |
| Abz287a | SEQ<br>ID<br>NO:<br>12 | QIQLVQSGAEVAKPGASVKVSCKASGYTFTRYTMHWVR<br>QRPGQGLEWIGYINPSRGYTNYNQKFKDRATLTTDKST<br>STAYMELSSLTSEDTAVYYCARYYDDHYCLDYWGQGTT<br>VTVSS |
| Abz494 | SEQ<br>ID<br>NO:<br>12 | QIQLVQSGAEVAKPGASVKVSCKASGYTFTRYTMHWVR<br>QRPGQGLEWIGYINPSRGYTNYNQKFKDRATLTTDKST<br>STAYMELSSLTSEDTAVYYCARYYDDHYCLDYWGQGTT<br>VTVSS |
| Abz495 | SEQ<br>ID<br>NO:<br>13 | QIQLVQSGAEVAKPGASVKVSCKASGYTFTRYTMHWVR<br>QRPGQGLEWIGYINPSHGYTNYNQKFKDRATLTTDKST<br>STAYMELSSLTSEDTAVYYCARYYDDHYCLDYWGQGTT<br>VTVSS |
| Abz497 | SEQ<br>ID<br>NO:<br>12 | QIQLVQSGAEVAKPGASVKVSCKASGYTFTRYTMHWVR<br>QRPGQGLEWIGYINPSRGYTNYNQKFKDRATLTTDKST<br>STAYMELSSLTSEDTAVYYCARYYDDHYCLDYWGQGTT<br>VTVSS |

It was further found by the inventors that preferable versions of histidine-mutated anti-CD3-epsilon antibody comprise one of the following light chain variable regions:

TABLE 4

Light chains of OKT3 and isolated acidic
pH-selective OKT3 variants:

|  |  |  |
|---|---|---|
| OKT3 | SEQ<br>ID<br>NO:<br>14 | QIVLTQSPAIMSASPGEKVTMTCSASSSVSYMNWYQQK<br>SGTSPKRWIYDTSKLASGVPAHFRGSGSGTSYSLTISG<br>MEAEDAATYYCQQWSSNPFTFGSGTKLEIK |
| Abz287a | SEQ<br>ID<br>NO:<br>15 | DIQLTQSPSSLSASVGDRVTITCRASSSVSYMNWYQQK<br>SGTAPKRWIYDTSKVASGVPYRFSGSGSGTSYTLTISS<br>LQPEDAATYYCQQWSSNPLTFGGGTKVEIK |
| Abz494 | SEQ<br>ID<br>NO:<br>16 | DIQLTQPPSSLSASVGDRVTITCRASSSVHYMNWYQQK<br>SGTAPKRWIYDTSKVASGVPYRFSGSGSGTSYTLTISS<br>LQPEDAATYYCQQWSSNPLTFGGGTKVEIK |
| Abz495 | SEQ<br>ID<br>NO:<br>15 | DIQLTQSPSSLSASVGDRVTITCRASSSVSYMNWYQQK<br>SGTAPKRWIYDTSKVASGVPYRFSGSGSGTSYTLTISS<br>LQPEDAATYYCQQWSSNPLTFGGGTKVEIK |
| Abz497 | SEQ<br>ID<br>NO:<br>17 | DIQLTQSPSSLSASVGDRVTITCRASSSVHYMNWYQQK<br>SGTAPKRWIYDTSKVASGVPYRFSGSGSGTSYTLTISS<br>LQPEDAATYYCQQWSSNPLTFGGGTKVEIK |

Preferable histidine-mutated anti-CD3-epsilon antibody according to the invention comprises any of the variable light chains as specified above and any one of the variable heavy chain domains as specified above.

TABLE 5

Light chains and heavy chains of isolated acidic
pH-selective OKT3 variants:

| pH-sensitive antibody | Heavy chain | Light chain |
|---|---|---|
| Abz494 | SEQ ID 12 | SEQ ID 16 |
| Abz495 | SEQ ID 13 | SEQ ID 15 |
| Abz497 | SEQ ID 12 | SEQ ID 17 |

A first preferred embodiment of the invention is a respectively histidine-mutated anti-CD3-epsilon antibody comprising the variable heavy chain sequence of Seq ID 12 and the variable light chain sequence of Seq ID 16.

A second preferred embodiment of the invention is a respectively histidine-mutated anti-CD3-epsilon antibody comprising the variable heavy chain sequence of Seq ID 13 and the variable light chain sequence of Seq ID 15.

A fourth preferred embodiment of the invention is a respectively histidine-mutated anti-CD3-epsilon antibody comprising the variable heavy chain sequence of Seq ID 12 and the variable light chain sequence of Seq ID 17.

In one embodiment histidine-mutated anti-CD3-epsilon antibody variants are a ScFv comprised of a light chain and a heavy chain recombinantly fused via an intervening peptide linker.

The histidine-mutated anti-CD3-epsilon antibody variants of the invention can be directly or indirectly linked to other molecules or by recombinant fusion with other polypeptides or proteins such as antibodies to cancer biomarkers. Techniques and methods to produce such antibody fusion proteins are well established in the art.

In a further aspect, the invention is directed to an isolated nucleic acid encoding: any one of the antibodies or antigen binding fragments of the invention, or any one of the polypeptides as defined above. The invention also encompasses an expression vector comprising such an isolated nucleic acid.

The invention also comprises a host cell comprising the antibody, binding fragment, polypeptide, polynucleotide or expression vector of the invention. Said host cell preferably is a *Pichia* cell or a Chinese hamster ovary cell.

The present invention also relates to a method of producing an antibody or antigen binding fragment comprising: (i) culturing a host cell comprising a polynucleotide encoding the heavy chain and/or the light chain of any one of the antibodies or antigen binding fragments of the invention under conditions favorable to expression of the polynucleotide; and (ii) optionally, recovering the antibody or antigen binding fragment from the host cell and/or culture medium.

In certain embodiments the host cell comprises an expression vector comprising such a polynucleotide, wherein the expression vector comprises control sequences operably linked to the polynucleotide which drive expression of the antibody or antigen binding fragment. In preferred embodiments, the polynucleotide comprises a secretion signal sequence which mediates secretion of the antibody or antigen binding fragment by the host cell.

The invention also provides pharmaceutical compositions suitable for the treatment of cancer diseases comprising histidine-mutated anti-CD3-epsilon antibody or a variant or an antigen binding fragment thereof, or a respective antibody-drug conjugate or an antibody cytokine fusion protein together with a pharmaceutically acceptable carrier, diluent or excipient.

The invention finally provides the therapeutic use of such histidine-mutated anti-CD3-epsilon antibody or biologically effective and active variant or fragment thereof, or ADCs or fusion proteins thereof, for the manufacture of a medicament for the treatment of solid-tumors as specified in detail below.

The histidine-mutated anti-CD3-epsilon antibody versions of the inventions exhibit the following advantageous properties and functions: the mutated anti-CD3-epsilon antibody and its variants do not bind to CD3 target, e.g., CD3 expressing cytotoxic T cells at neutral or physiological pH, thus avoiding on-target off-tumor T cell activation. The mutated anti-CD3-epsilon antibody and its variants show similar or improved binding to the target antigen at acidic pH, and the cross-linking activity of bispecific or multi-specific antibodies, in which mutated anti-CD3-epsilon antibody or its variants are a component remains only in acidic environments.

Upon binding to the membrane-bound target (human CD3 receptor on a T cell) T cell activation is initiated to trigger the cytotoxic activity of T-lymphocytes, irrespective of T-cell receptor specificity, major histocompatibility (MHC) restriction, or MHC down regulation on tumor cells (WU and CHEUNG 2018). Because the activation of T cells by engaging antibodies relies on neither high copy numbers of tumor surface antigen nor its intracellular trafficking, T-cell engaging antibodies may provide enhanced efficacy for cancer cells that express low levels of target antigen. In addition, due to multiple cytotoxic mechanisms, T cells engaged by cell-linking antibodies can potently target chemotherapy-resistant cancer cells and quiescent cancer stem cells (WU and CHEUNG 2018).

As the tumor microenvironment has an acidic pH, while normal tissues and non-cancerous cells have neutral pH, the T cell activation and associated cytotoxic activity of T-lymphocytes will occur only in tumor microenvironments, thereby reducing the on-target off-tumor side effects and allowing treatment dose escalation.

As activation of CD4+ and CD8+ T cells occurs through the simultaneous engagement of the T-cell receptor and a co-stimulatory molecule (like CD28, or ICOS) on the T cell by the major histocompatibility complex (MHCI and MHCII) peptide and co-stimulatory molecules on the APC, an antibody or antigen binding fragment of the invention is used in combination with agonists or ligand of CD28, or ICOS selected from a group of CD28 antibodies, CD80 (B7.1) and CD86 (B7.2) proteins and ICOS-L or compounds that induce expression of CD28 and ICOS ligand such as Toll-like receptor ligands (e.g. resiquimod) or immune checkpoint inhibitors such as CTLA-4 blockade, PD-1 inhibitors and PD-L1 inhibitors (e.g., Ipilimumab, Nivolumab and Atezolizumab).

The invention is also directed to a method of stimulating an immune response in a subject, comprising administering to a subject in need thereof the antibody or antigen binding fragment thereof of the invention in an amount effective to stimulate the immune response. Preferably, in such a method the antibody molecule is administered in combination with an agonist of one or more costimulatory molecules for example one or more molecules selected from the group consisting of OX40, CD2, CD27, CD28, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand. Alternatively, the antibody molecule is administered in combination with one or more inhibitors of an immune checkpoint molecule, for example one or more inhibitors selected from the group consisting of PD-1, PD-L1, PD-L2, TIM-3, LAG-3, CEACAM-1, CEACAM-5, VISTA, BTLA, TIGIT, LAIR1, CD160, 2B4 or TGFR In a further embodiment, the invention comprises a method of treating cancer wherein the cancer is selected from the group consisting of a lung cancer, a melanoma, a renal cancer, a liver cancer, a myeloma, a prostate cancer, a breast cancer, a colorectal cancer, a gastric cancer, a pancreatic cancer, a thyroid cancer, a hematological cancer, a lymphoma, a myeloma, or a leukemia, or a metastatic lesion of the cancer.

Also in relation to a method of treating cancer the invention also is directed to a method wherein the antibody molecule is administered in combination with one or more second therapeutic agents or procedures, for example wherein the second therapeutic agent or procedure is selected from the group consisting of chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy.

A further aspect of the present invention is a method of treating cancer in a subject, preferably a human subject, comprising administering to the subject an effective amount of the antibody or antigen binding fragment of the invention, or of an expression vector which mediates expression of the antibody or antigen binding fragment within the subject, optionally in association with a further therapeutic agent or therapeutic procedure.

T lymphocytes: A T cell is a type of lymphocyte, which develops in the thymus gland and plays a central role in the immune response. T cells can be distinguished from other lymphocytes by the presence of a T-cell receptor on the cell surface. These immune cells originate as precursor cells, derived from bone marrow, and develop into several distinct types of T cells once they have migrated to the thymus gland. T cell differentiation continues even after they have left the thymus.

Groups of specific, differentiated T cells have an important role in controlling and shaping the immune response by providing a variety of immune-related functions. One of these functions is immune-mediated cell death, and it is carried out by T cells in several ways: CD8+ T cells, also known as "killer cells", are cytotoxic—this means that they are able to directly kill virus-infected cells as well as cancer cells. CD8+ T cells are also able to utilize small signaling proteins, known as cytokines, to recruit other cells when mounting an immune response. A different population of T cells, the CD4+ T cells, function as "helper cells". Unlike CD8+ killer T cells, these CD4+ helper T cells function by indirectly killing cells identified as foreign: they determine if and how other parts of the immune system respond to a specific, perceived threat. Helper T cells also use cytokine signaling to influence regulatory B cells directly, and other cell populations indirectly. Regulatory T cells are yet another distinct population of these cells that provide the critical mechanism of tolerance, whereby immune cells are able to distinguish invading cells from "self"—thus preventing immune cells from inappropriately mounting a response against oneself (which would by definition be an "autoimmune" response). For this reason, these regulatory T cells have also been called "suppressor" T cells. These same self-tolerant cells are co-opted by cancer cells to prevent the recognition of, and an immune response against, tumor cells.

T cell receptor: The T-cell receptor (TCR) is a protein complex found on the surface of T cells, or T lymphocytes, that is responsible for recognizing fragments of antigens as peptides bound to major histocompatibility complex (MHC) molecules. The binding between TCR and antigen peptides is of relatively low affinity and is degenerate: that is, many TCRs recognize the same antigen peptide and many antigen peptides are recognized by the same TCR.

The T cell receptor exists as a complex of several proteins. The actual T cell receptor is composed of two separate peptide chains, which are produced from the independent T cell receptor alpha and beta (TCRα and TCRβ) genes. The other proteins in the complex are the CD3 proteins: CD3εγ and CD3εδ heterodimers and, most important, a CD3ζ homodimer, which has a total of six ITAM motifs. The ITAM motifs on the CD3ζ can be phosphorylated by Lck and in turn recruit ZAP-70. Lck and/or ZAP-70 can also phosphorylate the tyrosines on many other molecules, not least CD28, LAT and SLP-76, which allows the aggregation of signalling complexes around these proteins.

CD3 receptor: CD3 (cluster of differentiation 3) is a protein complex and T cell co-receptor that is involved in activating both the cytotoxic T cell (CD8+ naive T cells) and T helper cells (CD4+ naive T cells). It is composed of four distinct chains. In mammals, the complex contains a CD3γ chain, a CD3δ chain, and two CD3ε chains. These chains associate with the T-cell receptor (TCR) and the ζ-chain (zeta-chain) to generate an activation signal in T lymphocytes. The TCR, ζ-chain, and CD3 molecules together constitute the TCR complex.

T cell activation: Activation of CD4+ T cells occurs through the simultaneous engagement of the T-cell receptor and a co-stimulatory molecule (like CD28, or ICOS) on the T cell by the major histocompatibility complex (MHCII) peptide and co-stimulatory molecules on the APC. Both are required for production of an effective immune response; in the absence of co-stimulation, T cell receptor signaling alone results in anergy.

T cell engaging antibodies bound to target cells are known to trigger the cytotoxic activity of T-lymphocytes by cross-linking to CD3, irrespective of T-cell receptor specificity, major histocompatibility (MHC) restriction, or MHC down regulation on tumor cells (WU and CHEUNG 2018). Because the activation of T cells by engaging antibodies relies on neither high copy numbers of tumor surface antigen nor its intracellular trafficking, T-cell engaging antibodies may provide enhanced efficacy for cancer cells that express low levels of target antigen. In addition, due to multiple cytotoxic mechanisms, T cells engaged by cell-linking antibodies can potently target chemotherapy-resistant cancer cells and quiescent cancer stem cells (WU and CHEUNG 2018). Activated T cells express surface receptors, such as CD25 (the IL-2 receptor) or co-stimulatory molecules such as CD28 (SHIPKOVA and WIELAND 2012). Thus these surface receptors can be used to assess T-cell activation by flow cytometry.

OKT3: OKT3 or Muromonab-CD3 is murine monoclonal antibody, targeting the CD3 receptor, a membrane protein on the surface of T cells. In 1985, it was the first monoclonal antibody to be approved for clinical use in humans as an immunosuppressant drug given to reduce acute rejection in patients with organ transplants. It binds to the T cell receptor-CD3-complex (specifically the CD3 epsilon chain) on the surface of circulating T cells, initially leading to an activation. OKT3 variants are widely used in construction of bispecific and multi-specific T cell engaging antibodies to cross-link cytotoxic T cells to cancer cells.

The sequences which are important in view of the present invention are listed below in detail:
OKT3 Light Chain Sequence Variable Region (VL) SEQ ID 14;
OKT3 Heavy Chain Sequence Variable Region (VH) SEQ ID 11;
Humanized OKT3 Light Chain Sequence Variable Region (VL) SEQ ID 15;
Humanized OKT3 Heavy Chain Sequence Variable Region (VH) SEQ ID 12;
OKT3 CDR1 Sequence of VL SEQ ID 5;
OKT3 CDR2 Sequence of VL SEQ ID 8;
OKT3 CDR3 Sequence of VL SEQ ID 9;
OKT3 CDR1 Sequence of VH SEQ ID 1;
OKT3 CDR2 Sequence of VH SEQ ID 2;
OKT3 CDR3 Sequence of VH SEQ ID 4.

In addition to the use for the therapy of acute, glucocorticoid-resistant rejection of allogeneic renal, heart and liver transplants approved in many countries, OKT3 variants are widely used in bispecific and multi-specific T-cell engaging antibodies to cross-link cytotoxic T cells to cancer cells (HUEHLS et al. 2015). The anti-CD3 arm in Blincyto® (Blinatumomab) approved for treatment of refractory acute lymphoblastic leukemia is also derived from OKT3. Therefore, the histidine-mutated OKT3 versions according to the invention are applicable in the treatment of cancer, and other diseases in which T cell cytotoxicity is involved.

The invention can further be described with respect to additional variable chain sequences from monoclonal antibodies specific for CD3, including:

```
UTCH1 Heavy Chain Variable Region (mouse
antibody);
                                      SEQ ID NO: 23
EVQLQQSGPELVKPGASMKISCKASGYSFTGYTMNWVKQSHGKNLEWMGL

INPYKGVSTYNQKFKDKATLTVDKSSSTAYMELLSLTSEDSAVYYCARSG

YYGDSDWYFDVWGQGTTLTVFS

UTCH1 Light Chain Variable Region;
                                      SEQ ID NO: 24
DIQMTQTTSSLSASLGDRVTISCRASQDIRNYLNWYQQKPDGTVKLLIYY

TSRLHSGVPSKFSGSGSGTDYSLTISNLEQEDIATYFCQQGNTLPWTFAG

GTKLEIK

SP34 fusion sequence including Light and Heavy
Chain Variable Regions;
                                      SEQ ID NO: 25
EVQLVESGGGLVQPGGSLKLSCAASGFTFNKYAMNWVRQAPGKGLEWVAR

IRSKYNNYATYYADSVKDRFTISRDDSKNTAYLQMNNLKTEDTAVYYCVR

HGNFGNSYISYWAYWGQGTLVTVSSGGGGSGGGGSQTVVTQEPSLTVSPG

GTVTLTCGSSTGAVTSGYYPNWVQQKPGQAPRGLIGGTKFLAPGTPARFS

GSLLGGKAALTLSGVQPEDEAEYYCALWYSNRWVFGGGTKLTVLGQP
```

The UTCH1 antibody is described in Wauwe et al., Cell Immunol. 86(2) 525-34, 1984 (pubmed.ncbi.nlm.nih.gov/6234071), the contents of which are incorporated herein by reference. The SP34 antibody is described in Conrad et al., Cytometry A (71(11): 925-33, 2007 (pubmed.ncbi.nlm.nih-.gov/17654651/), the contents of which are incorporated herein by reference.

An anti-CD3ε antibody described in the state of the art is SP34 (Yang S J, The Journal of Immunology (1986) 137; 1097-1100). SP34 reacts with both primate and human CD3. SP34 is available from Pharmingen. A further anti-CD3 antibody described in the state of the art is UCHT-1 (see WO2000041474). A further anti CD3 antibody described in the state of the art is BC-3 (Fred Hutchinson Cancer Research Institute; used in Phase I/II trials of GvHD, Anasetti et al., Transplantation 54: 844 (1992))(available from BioLegend, San Diego, CA). SP34 differs from UCHT-1 and BC-3 in that SP-34 recognizes an epitope present on solely the ε chain of CD3 (see Salmeron et al., (1991) J. Immunol. 147: 3047) whereas UCHT-1 and BC-3 recognize an epitope contributed by both the ε and γ chains. An antibody with the same sequence as of antibody SP34 is mentioned in WO2008119565, WO2008119566, WO2008119567, WO2010037836, WO2010037837 and WO2010037838. An antibody VH which is 96% identical to VH of antibody SP34 is mentioned in U.S. Pat. No. 8,236,308 (WO2007042261).

All citations respecting the description of these antibodies is incorporated herein by reference in their entirety.

For commercially available antibodies, one of skill can obtain the sequence and identify the variable regions and the CDRs.

Selection of Antibodies

Selection of suitable anti-CD3 antibody versions of OKT3 and fragments thereof according to the invention may be achieved by well-established and known methods and techniques in the art, such as by histidine substitution via phage display libraries or from combinatorial histidine substitution libraries by yeast surface display. Details are provided in the Example section.

Terms, Definitions

The term "antibody" or "immunoglobulin" is used according to the invention in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity. Depending on the amino acid sequence of their constant regions, intact or whole antibodies can be assigned to different classes. There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2.

"Antibody fragments" according to the invention comprise a portion of an intact antibody, preferably comprising the antigen-binding or variable region thereof. Examples of antibody fragments include Fab, Fab', F(ab')2, Fv, single chain Fv (scFV) and Fc fragments, diabodies, linear antibodies, single-chain antibody molecules; bispecific and multispecific antibodies formed from antibody fragment(s).

Preferred monovalent antibody fragments for antibodies according to the invention is ScFV or Fab.

A "whole or complete" antibody according to the invention is an antibody which comprises an antigen-binding variable region as well as a light chain constant domain (CL) and heavy chain constant domains, CH1, CH2 and CH3.

A "Fc" region of an antibody according to the invention comprises, as a rule, a CH2, CH3 and the hinge region of an IgG1 or IgG2 antibody major class. The hinge region is a group of about 15 amino acid residues which combine the CH1 region with the CH2-CH3 region.

A "Fab" fragment also contains the constant domain of the light chain and the first constant domain (CH1) of the heavy chain and has one antigen-binding site only.

"Fab'" fragments differ from Fab fragments by the addition of a few residues at the carboxy-terminus of the heavy chain CH1 domain including one or more cysteine residues from the antibody hinge region.

A "F(ab')2" antibody according to this invention is produced as pairs of Fab' fragments which have hinge cysteines between them.

"Single-chain FV" or "scFv" antibody fragments according to the invention comprise the VH, and VL, domains of antibody, wherein these domains are present in a single polypeptide chain. Preferably, the Fv polypeptide further comprises a polypeptide linker between the VH and VL domains which enables the scFv to form the desired structure for antigen binding.

The "variable domain" of an antibody according to the invention comprises the framework regions (usually FR1 to FR4) as well as the CDR domains (usually CDR1, CDR2 and CDR3) which are designated as "hypervariable regions".

The term "hypervariable region" or "CDR" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain.

If not otherwise pointed out, the amino acid positions within the antibody molecules according to this invention are numbered according to Kabat.

"Framework Region" or "FR" residues are those variable domain residues other than the hypervariable region residues as herein defined.

"Antibody variants" according to the invention include antibodies that have a modified amino acid sequence compared to the parental antibody but have the same or changed binding affinity to the targeted antigen. Antibody variants differ from the parental antibody by replacement or deletion or addition of one or more amino acid residues at specific positions within the variable domains, including the CDR domains, and/or the constant regions of the antibody, in order to modify certain properties of the antibody, such as binding affinity and/or receptor functions, e.g., ADCC, FcRn binding and the like. The histidine-mutated antibodies of this invention without further modifications are not designated as "antibody variants" according to this invention. Antibody variants according to the invention exhibit a sequence homology of 80-99% compared to the parental antibody, preferably 90%, 91%, 92%, 93%, 94%, 95%, 96%, 97%, 98% and 99%, dependent on the specific location of the amino acid residue to be replaced, deleted or added.

The term "fusion protein" refers to a natural or synthetic molecule consisting of one or more biological molecules as defined above, wherein two or more peptide- or protein-based (glycoproteins included) molecules having different specificity are fused together optionally by chemical or amino acid-based linker molecules. The linkage may be achieved by C—N fusion or N—C fusion (in 5'.-.3' direction), preferably C—N fusion. A fusion protein according to the invention is fusion of said antibody or antibody variant of this invention to another antibody or protein, preferably an antibody to tumor-associated antigen.

The term "antibody-drug conjugate (ADC)" refers according to the invention to an immunoconjugate composed of an antibody, preferably complete antibody, according to the invention, and a preferably chemical cytotoxic agent. The components are chemically attached to each other by specific linkers. The antibody of the invention (preferably within its heavy chain constant region) may be modified at one or more amino acid positions in order to create a suitable linkage to the linker and/or the cytotoxic payload drug. Method and techniques to generate such ADCs are well known in the art.

The term "cytokine" is a generic term for proteins released by one cell population which act on another cell as intercellular mediators. Examples of such cytokines are lymphokines, monokines, and traditional polypeptide hormones, such as vascular endothelial growth factor (VEGF); integrins thrombopoietin (TPO); nerve growth factors such as NGF.beta; platelet-growth factor; transforming growth factors (TGFs) such as TGF.alpha. and TGF.beta; erythropoietin (EPO); interferons such as IFN.alpha., IFN.beta., and IFN.gamma; colony stimulating factors such as M-CSF, GM-CSF and G-CSF; interleukins such as IL-1, IL-1a, IL-2, IL-3, IL-4, IL-5, IL-6, IL-7, IL-8, IL-9, IL-10, IL-11, IL-12, and TNF-.alpha. or TNF-beta.

The term "biologically/functionally effective" or "therapeutically effective (amount)" refers to a drug/molecule which causes a biological function or a change of a biological function in vivo or in vitro, and which is effective in a specific amount to treat a disease or disorder in a mammal, preferably in a human.

The term "pharmaceutical treatment" means a variety of modalities for practicing the invention in terms of the steps. For example, the agents according to the invention can be administered simultaneously, sequentially, or separately. Furthermore, the agents can be separately administered within one or more time intervals between administrations. Therapeutic compositions of the present invention contain a physiologically tolerable carrier together with the relevant agent as described herein, dissolved or dispersed therein as an active ingredient.

As used herein, the term "pharmaceutically acceptable" refers to compositions, carriers, diluents and reagents which represent materials that are capable of administration to or upon a mammal without the production of undesirable physiological effects such as nausea, dizziness, gastric upset and the like. The preparation of a pharmacological composition that contains active ingredients dissolved or dispersed therein is well understood in the art and need not be limited based on formulation. Typically, such compositions are prepared as an injectable preparation either as liquid solutions or suspensions, however, solid forms suitable for solution, or suspensions, in liquid prior to use can also be prepared. The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which may enhance the effectiveness of the active ingredient. The therapeutic composition of the present invention can include pharmaceutically acceptable salts of the components therein.

The histidine-mutated anti-CD3-epsilon antibody versions according to the invention are suitable for the treatment of the same disorders and diseases as the approved and marketed non-histidine mutated anti-CD3-epsilon antibody which is Muromonab-CD3 is approved for the therapy of acute, glucocorticoid-resistant rejection of allogeneic renal, heart and liver transplants and cancer, wherein the drug is preferably administered by subcutaneous or systemic injection.

Like the marketed drug, the histidine-mutated OKT3 according to the invention can be used alone or in combination with other drugs which support the therapy, such as methotrexate, DMARDS, glucocorticoids, nonsteroidal anti-inflammatory drugs (NSAIDs), and/or analgesics.

Specific embodiments according to the methods of the present invention will now be described in the following examples. The examples are illustrative only, and are not intended to limit the remainder of the disclosure in any way.

Example 1: His-Scanning Combinatorial Library Design

The crystal structure of the human T cell receptor CD3 epsilon/gamma heterodimer complexed to the therapeutic mAb OKT3 (KJER-NIELSEN et al. 2004) has identified the interacting amino acid residues of OKT3 CDRs with human CD3 epsilon. 5 interacting residues in the light chain and 9 interacting residues in the heavy chain of OKT3 have been identified or in total there are 14 amino acid residues of OKT3 that are in contact with CD3 epsilon receptor. All but one antigen-interacting residues are located in antibody CDRs (FIG. 1). Antigen-interacting residues are underlined.

Example 2: Yeast Surface Display Combinatorial Library

Anti-CD3 in the scFv format is widely used in construction of bispecific T cell engaging antibodies. ScFv anti-CD3 was used in therapeutic T cell cross-linking antibody Blincyto and in more than 50 bispecific T cell engaging antibodies in clinical trials (SUURS et al. 2019) as well as other constructs in pre-clinical stages (IIZUKA et al. 2019; BANASZEK et al. 2019; ELLERMAN 2019). Histidine-scanning combinatorial ScFV libraries consisting of humanized OKT3 heavy and light chain variable regions are synthesized by Gene Universal (Delaware, USA), where each interacting amino acid residue in the OKT3 CDRs remains or is replaced with histidine at a 1:1 ratio. There are theoretically 2^14 or 16,384 possible combinations in this histidine-scanning combinatorial library. It would be extremely labor-intensive and time-consuming to synthesize all 16,384 gene constructs, produce respective antibody variants and validate each one for its pH-sensitive target binding activity.

It is noted that the crystal structure of the human T cell receptor CD3 epsilon/gamma heterodimer complexed to another anti-CD3 antibody UCHT1 is also available (ARNETT et al. 2004); with a similar approach one could design and make similar UCHT1-based histidine-scanning combinatorial libraries.

The ScFV histidine-scanning combinatorial library was cloned into a yeast display vector (plasmid p497) by transformation associated gap-repair (ORR-WEAVER et al. 1983) in yeast strain A169 (Mat alpha GalI p-AGA1/URA3 ura3-52 trp1::NatMX leu2-Δ200 his3-Δ200 lys2Δ pep4::ZeoR prbΔ1.6R can1 ung1::HygB ham1::KanMX). As a result, the OKT3 scFV variants were expressed as a fusion protein to the C-terminus of yeast membrane-anchor protein AGA2. The resulting construct will have AGA2 in the N-terminus, followed by ScFV and an HA tag at the C-terminus. More than 10^7 transformants were obtained. Display of the ScFV histidine-scanning ScFv library on the yeast cell surface was confirmed by cytoflow analysis monitoring expression of the HA tag. Corresponding parental ScFv was also displayed on the yeast cell surface and served as a control.

Example 3: Isolation of Anti-CD3 Antibodies Binding Preferentially to Human CD3 at Acidic pH Over Physiological pH This Example describes the generation of antibodies that bind preferentially to human CD3 at low (acidic) pH relative to neutral or physiological pH. FIG. 2 presents experimental steps for isolation of anti-CD3 antibodies that bind preferentially to human CD3 at acidic pH.

Figure 3B:
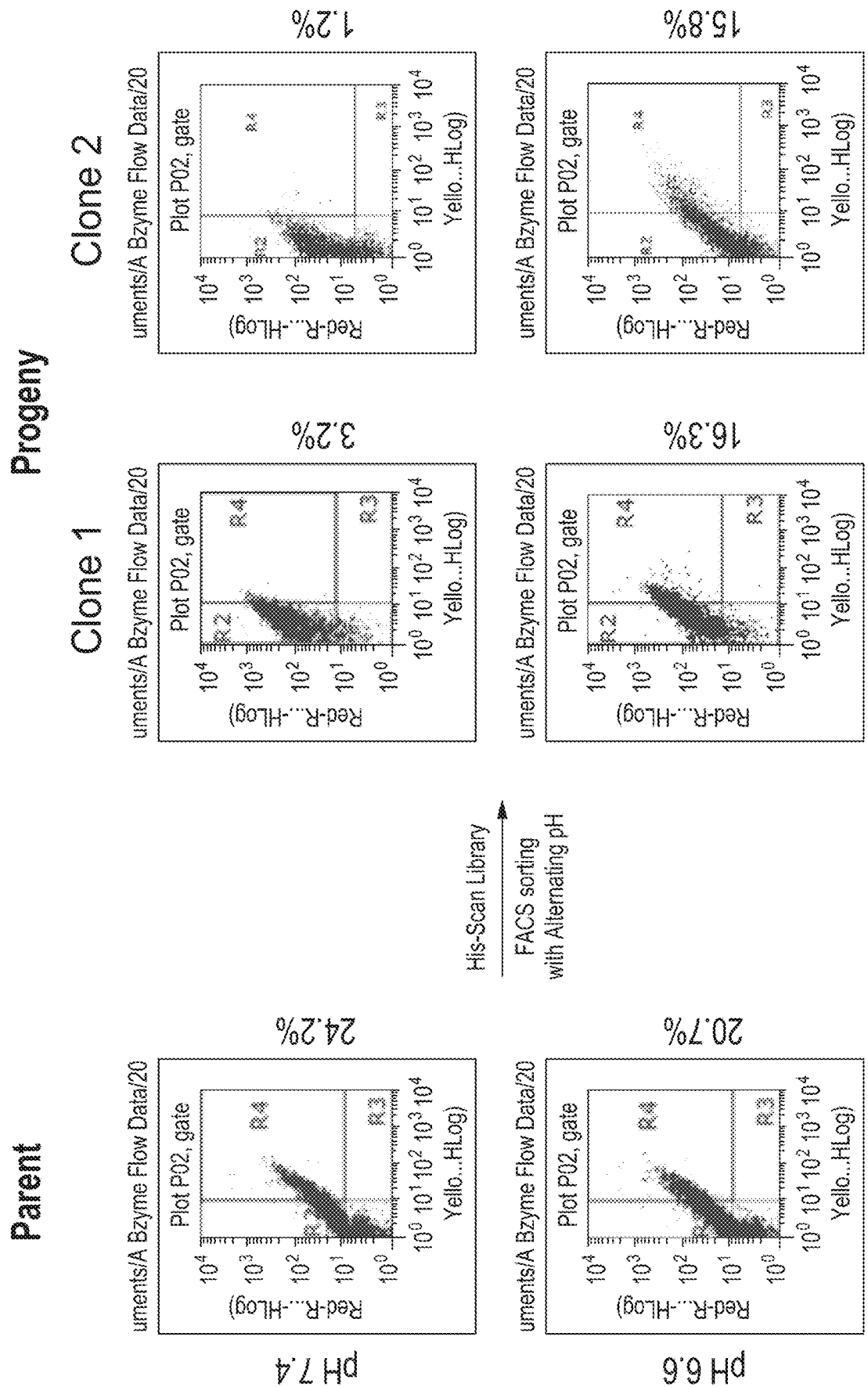
FIG. 3B. Single clone analysis of yeast cells sorted by FACS to identify clones that bind to the target at acidic pH, but not at neutral pH.

Transformants were expressed in yeast selective media supplemented with galactose as a sole carbon source to induce expression of the AGA2-ScFV fusion constructs. ScFV-expressing cells were stained with biotinylated CD3 epsilon at the acidic pH 6.2. Subsequently, cells that carried ScFv anti-CD3 variants were enriched over three rounds of FACS sorting. In the last sorting, cells were incubated with naked CD3 epsilon/delta heterodimers at pH6.2, followed by washing at pH7.4 to wash way unbound antigens and antigens from weakly bound cells at pH7.4. Those cells free from antigens were stained with biotinylated CD3 at acidic pH and sorted by FACS. FIG. 3a presents an example of FACS sorting to isolate a subpopulation of yeast cells displaying anti-CD3 scFV that bind preferentially to human CD3 at acidic pH. Individual yeast colonies yeast subpopulation sorted by FACS were subjected to cytoflow analysis for binding to the target antigen at pH6.2 and pH7.4. FIG. 3b presents an example of cytoflow analysis of yeast clones expressing anti-CD3 scFV that bind preferentially to human CD3 at acidic pH.

Example 4: Mutation Nature of pH-Dependent Antibodies

Figure 4:
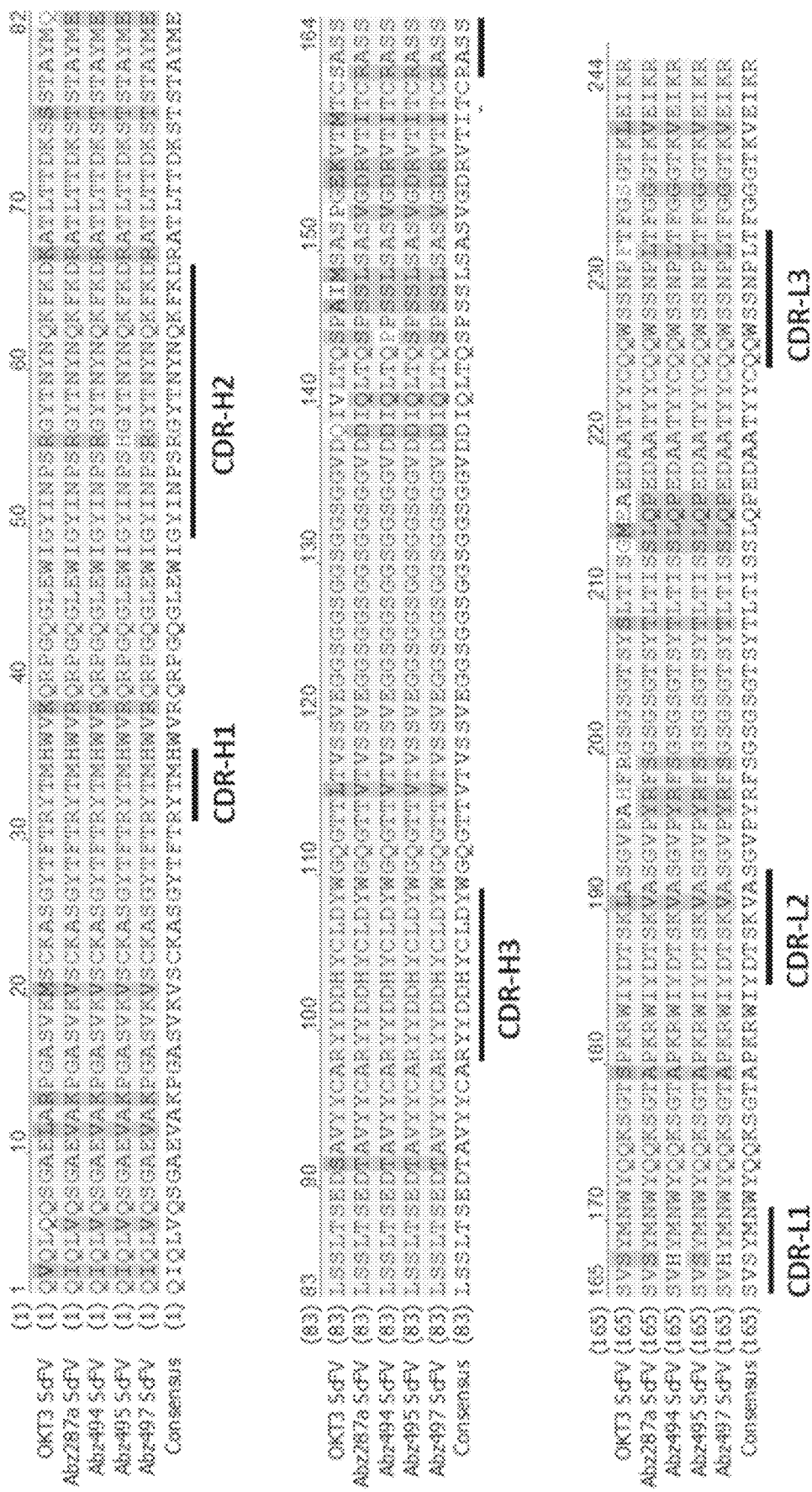
FIG. 4: Aligned protein sequences of parental OKT3 derived parental ScFV with unique sequences of isolated pH-sensitive ScFV after three rounds of selection followed by cytoflow analysis of single clones. The sequences shown in the figure are, sequentially, SEQ ID NO:18 (OKT3 ScFV), SEQ ID NO:19 (Abz287a ScFV), SEQ ID NO:20 (Abz494), SEQ ID NO:21 (Abz495), and SEQ ID NO:22 (Abz497). The consensus sequence has the same sequence as Abz287a (SEQ ID NO:19).
Figure 5A:
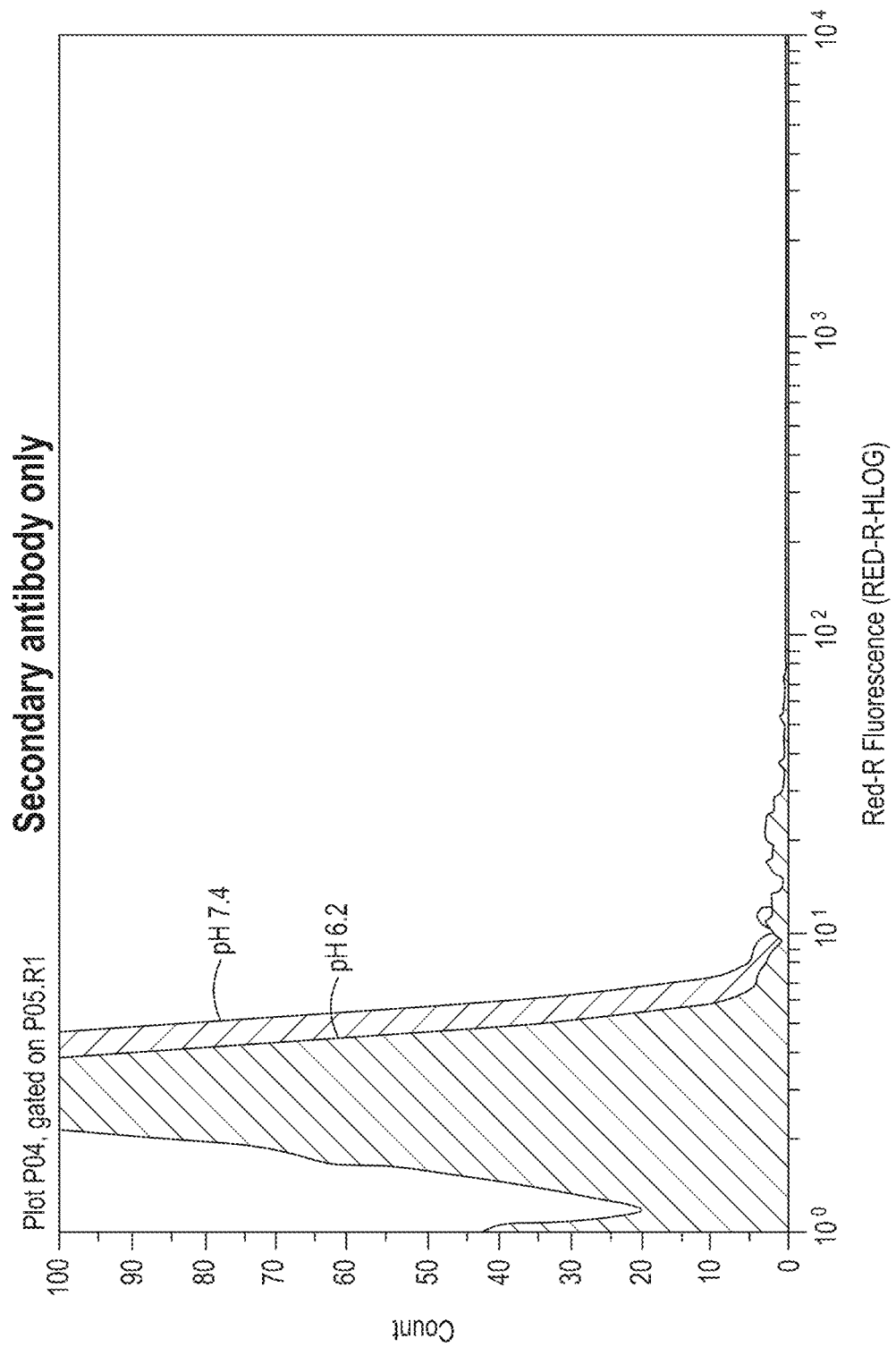
FIGS. 5A to 5E: Differential binding of mutated ScFV variants of OKT3 to Jurkat cells at acidic and neutral pH.
Figure 5B:
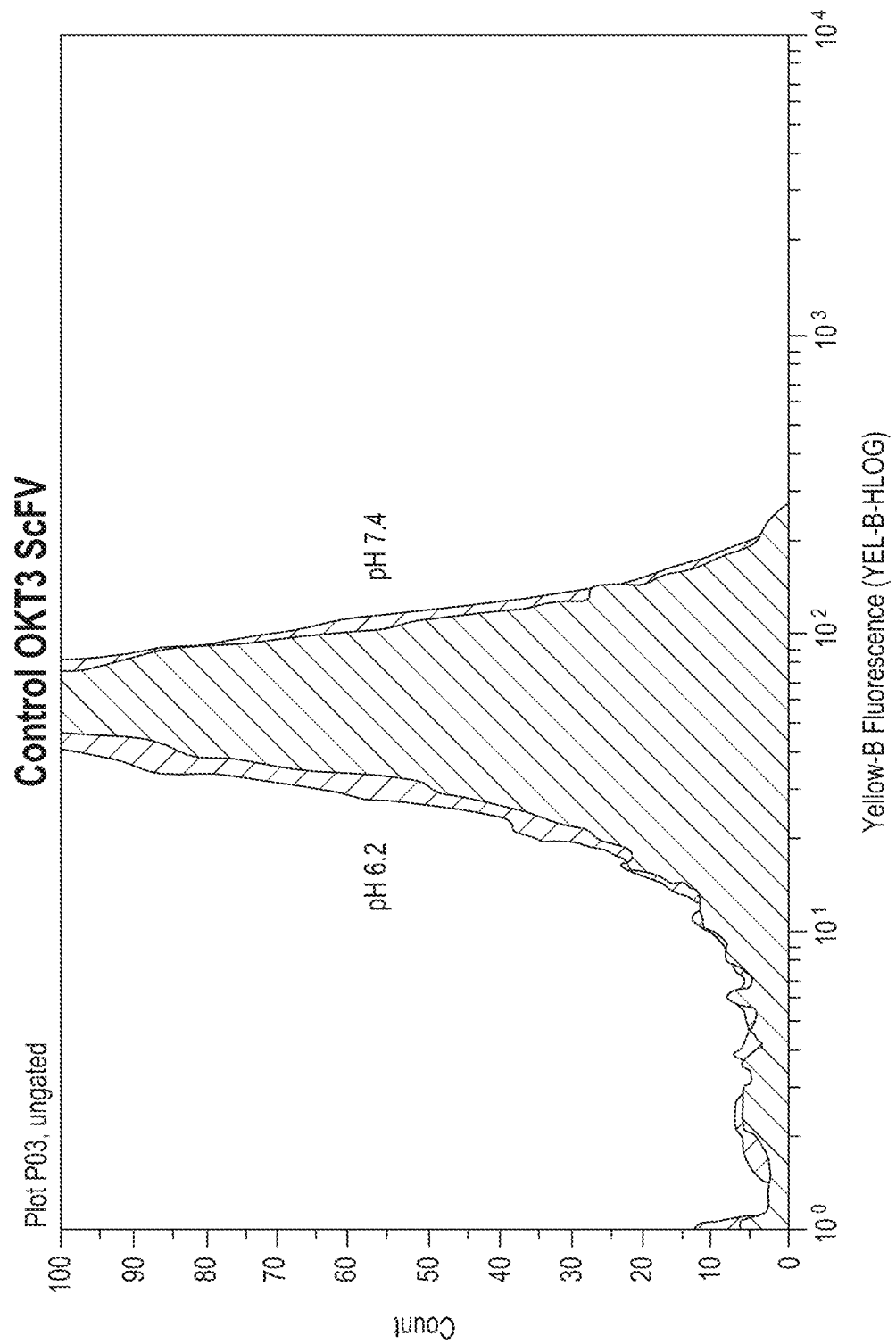
Figure 5C:
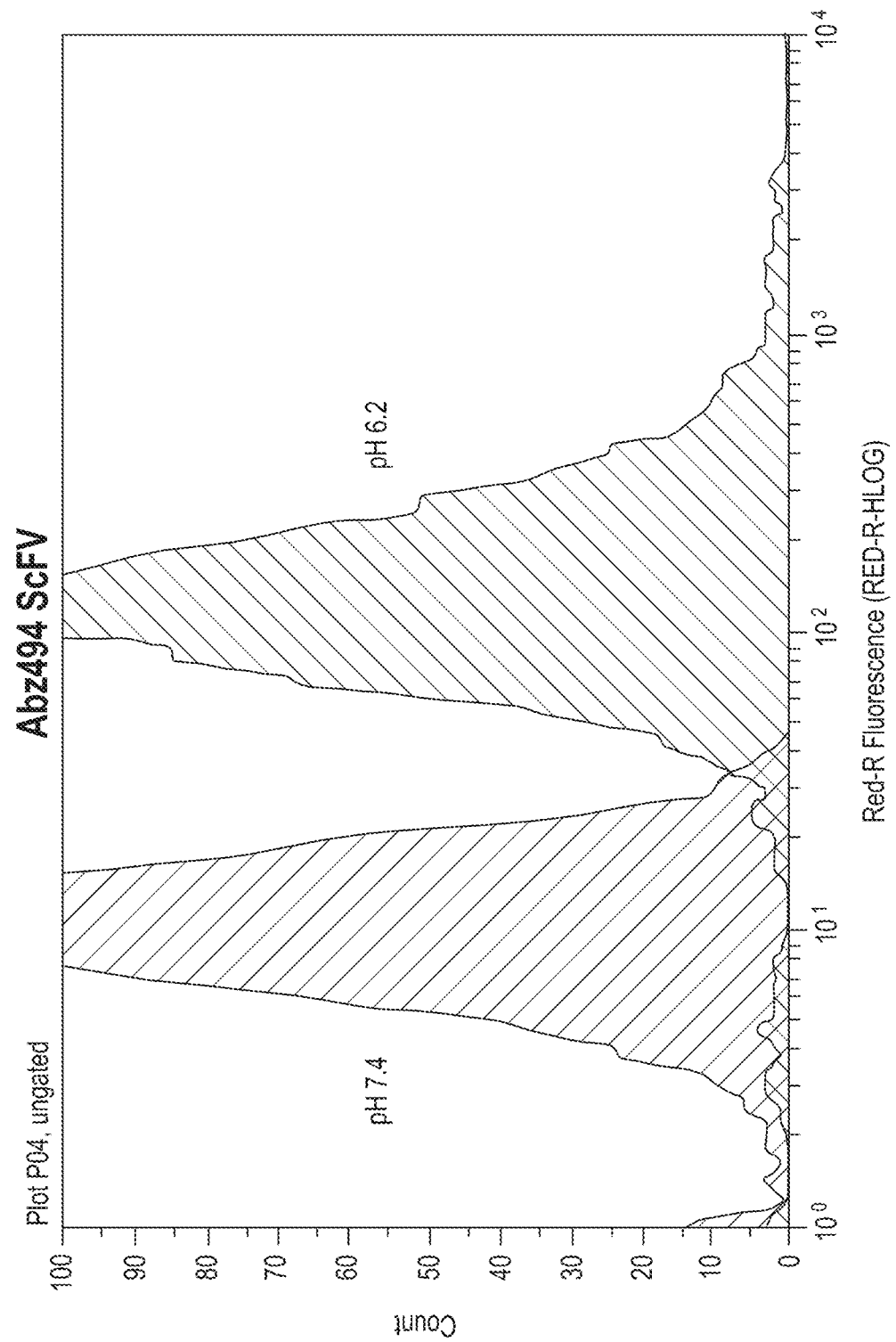
Figure 5D:
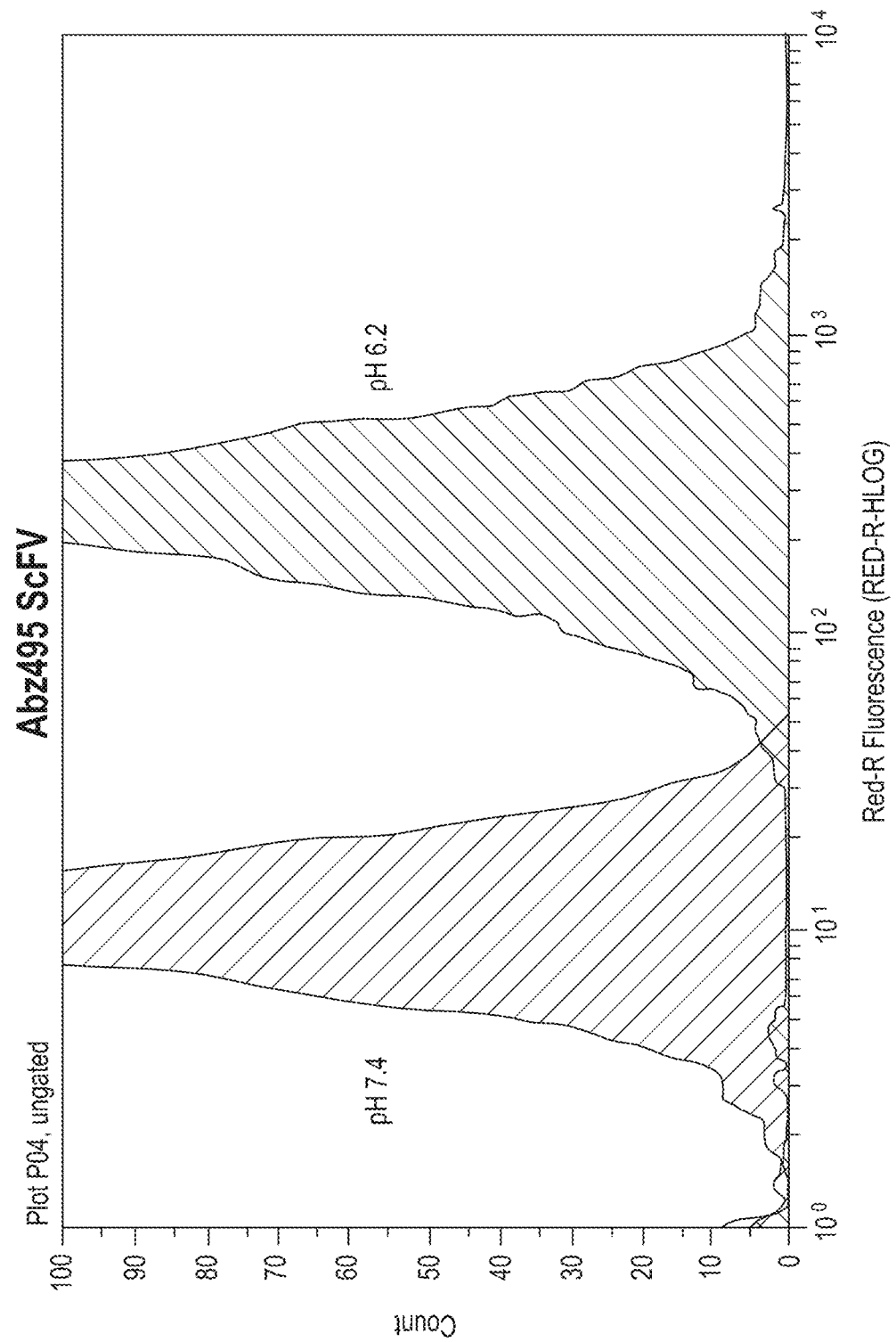
Figure 5E:
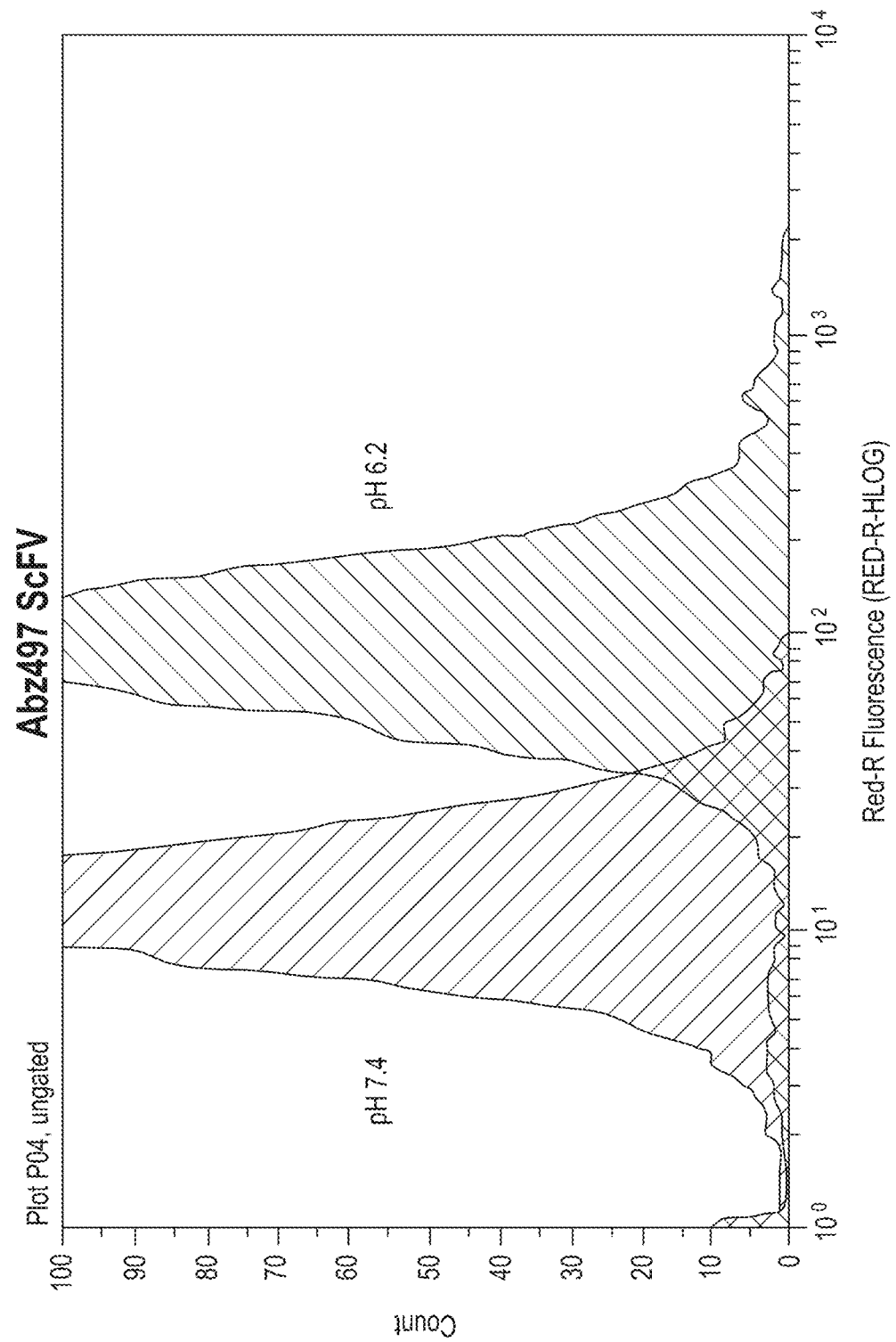

Yeast clones expressing antibodies that bind significantly to CD3 at acidic pH, but none or reduced binding at neutral pH were selected. Anti-CD3 ScFv from selected yeast clones were sequenced to identify mutations. Analysis of amino acid sequences revealed the histidine substitutions occurred in CDR regions. The number of histidine mutations ranged from one such as in Abz495 to eight substitutions as in Abz496 and Abz498. FIG. 4 presents a protein alignment of scFV of derived from OKT3, humanized scFV OKT3 and three selected pH-dependent humanized variants—Abz494, Abz495 and Abz497 that subsequently have been validated for preferential binding to human CD3 on cell surface at acidic pH in Example 5. Compared to the humanized scV OKT3 (Abz287a), the Abz495 variant has R to H substitution in the CDR-H2, while both Abz494 and Abz497 variants have a S to H substitution in CDR-L1. Abz494 has an additional S to P substitution in light chain framework 1.

Example 5: pH-Dependent CD3 Antibodies Bind Preferentially to Human CD3 Receptor on Human Cells at Acidic pH This Example describes the characterization of antibodies that bind preferentially to human CD3 receptor on human cells at low (acidic) pH relative to neutral or physiological pH in flow cytometry. The inventors have shown that antibodies bind strongly to the CD3 receptor target at acidic pH 6.2, but none or significantly reduced binding at neutral or physiological pH 7.4 CD3+ cell flow cytometry assays. ATCC human lymphoblast-derived Jurkat cells, clone E6-1 is known to express CD3 receptor (ATCC cat #TIB-152). Jurkat cells grown in RPMI-1640 Medium were stained with either OKT3 scFv antibody control or pH-dependent ScFV antibody variants (Abz494, Abz495 and Abz497) in either acidic or neutral pH buffers. FIGS. 5A to 5E present the cytoflow analysis of Jurkat cells stained with various anti-CD3 antibodies at various pHs. While the parental OKT3 antibody has similar bindings to the CD3, pH-dependent variants show strong binding to the CD3 receptor at acidic pH 6.2 while significantly reduced binding at neutral pH 7.4.

Example 6: pH-Selective Antibodies in T Cell Activation in Acidic and Neutral pHs This Example describes the ability of acidic pH-selective antibodies in activating T cells in neutral and acidic pH compared to parental antibodies.

Human PBMCs were distributed in 2, 12-well plates at a density of 2×106 cells per well at 2 mL media per well (RPMI-1640 media, 10% FBS, 1% Pen/Strep) and incubated for 24 hours. After 24 hours, the media was changed; one plate containing media at a pH of 7.4 and the other at a pH of 6.2. Each well was treated with either one wildtype anti-CD3 OKT3 scFV or one of 3 pH-dependent anti-CD3 ScFVs (Abz494, Abz495, and Abz497). As all scFV antibodies contain FLAG tag at the C termini, mouse monoclonal anti-FLAG IgG antibodies were added to cross-link FLAG-tagged scFVs. It has been shown that in the acidic condition, in the absence of co-stimulant such as CD28 agonist (BOSTICARDO et al. 2001), anti-CD3 antibodies failed to activate T cells. Therefore, there is the need of co-stimulant (CD28 agonist) in T cell activation in acidic pH. After 24 hour and 48 hour incubations, cells were stained with either biotinylated antibodies against CD25 or CD28 to measure T cell activation using flow cytometry.

TABLE 6

T cell activation after exposed to Abz495/anti-FLAG monitored by expression of CD28:

| Test antibodies | pH 6.2 | | pH 7.4 | |
| --- | --- | --- | --- | --- |
| | CD25 | CD28 | CD25 | CD28 |
| Control-OKT3 ScFV | 2.35 | 5.15 | 8.1 | 6.88 |
| Test antibody-Abz495 | 2.28 | 5.0 | 1.0 | −0.64 |

Note:
Percentage of receptor display after subtraction of the background in the well treated with anti-FLAG IgG antibodies only.

Example 7: Further Engineering of Acidic pH-Selective Antibodies to Cross-Link Cancer Cells to T Cells This Example describes how to further engineer acidic pH-selective antibodies to activate the T cells in the presence of respective cancer cells. Example 5 has shown that pH-dependent anti-CD3 antibodies preferentially bind to CD3 receptor on cell surface at acidic pH. Example 6 showed that these antibody variants have reduced T-cell activation activities compared to the wild type, while have comparable activity at acidic pHs. One can design bispecific antibodies to cross-link host T cells to cancer cells activating T cells at acidic pH while have reduced activity at neutral pHs. For example, a bi-specific antibody consisting of an anti-HER2 Fab fused with pH-dependent anti-CD3 scFV fused to Fab at the C-terminus of the Fab light chain or heavy chain in T cell activation in acidic conditions. It is known that biased activation of human T lymphocytes due to low extracellular pH is antagonized by B7/CD28 co-stimulation (BOSTICARDO et al. 2001), anti-CD28 agonist antibody may be added. Human PBMC and Her2 expressing cancer cells (SKBR3, Her2 3+, MDA MB453, Her2 2+; MDA MB231, Her2 1+; MDA MB468, Her2 0 or HER2 negative) may be co-cultured in the presence of various concentrations of CD3× HER2 bispecific antibodies. Activation of T cells can be monitored by measuring the amount of IL-2 produced or expression level of CD25 or CD28 on activated T cells.

CITATIONS

ARNETT, K. L., S. C. HARRISON and D. C. WILEY, 2004 Crystal structure of a human CD3-epsilon/delta dimer in complex with a UCHT1 single-chain antibody fragment. Proc Natl Acad Sci USA 101: 16268-16273.

BAEUERLE, P. A., and C. REINHARDT, 2009 Bispecific T-cell engaging antibodies for cancer therapy. Cancer Res 69: 4941-4944.

BANASZEK, A., T. G. P. BUMM, B. NOWOTNY, M. GEIS, K. JACOB et al., 2019 On-target restoration of a split T cell-engaging antibody for precision immunotherapy. Nat Commun 10: 5387.

BOSTICARDO, M., S. ARIOTTI, G. LOSANA, P. BERNABEI, G. FORNI et al., 2001 Biased activation of human T lymphocytes due to low extracellular pH is antagonized by B7/CD28 costimulation. Eur J Immunol 31: 2829-2838.

BRETSCHER, P. A., 1999 A two-step, two-signal model for the primary activation of precursor helper T cells. Proc Natl Acad Sci USA 96: 185-190.

CHAPARRO-RIGGERS, J., H. LIANG, R. M. DEVAY, L. BAI, J. E. SUTTON et al., 2012 Increasing serum half-life and extending cholesterol lowering in vivo by engineering antibody with pH-sensitive binding to PCSK9. J Biol Chem 287: 11090-11097.

ELLERMAN, D., 2019 Bispecific T-cell engagers: Towards understanding variables influencing the in vitro potency and tumor selectivity and their modulation to enhance their efficacy and safety. Methods 154: 102-117.

ESTRELLA, V., T. CHEN, M. LLOYD, J. WOJTKOWIAK, H. H. CORNNELL et al., 2013 Acidity generated by the tumor microenvironment drives local invasion. Cancer Res 73: 1524-1535.

GERA, N., A. B. HILL, D. P. WHITE, R. G. CARBONELL and B. M. RAO, 2012 Design of pH sensitive binding proteins from the hyperthermophilic Sso7d scaffold. PLoS One 7: e48928.

GERWECK, L. E., and K. SEETHARAMAN, 1996 Cellular pH gradient in tumor versus normal tissue: potential exploitation for the treatment of cancer. Cancer Res 56: 1194-1198.

HARGUINDEY, S., and S. J. RESHKIN, 2017 "The new pH-centric anticancer paradigm in Oncology and Medicine"; SCB, 2017. Semin Cancer Biol 43: 1-4.

HUEHLS, A. M., T. A. COUPET and C. L. SENTMAN, 2015 Bispecific T-cell engagers for cancer immunotherapy. Immunol Cell Biol 93: 290-296.

IGAWA, T., S. ISHII, T. TACHIBANA, A. MAEDA, Y. HIGUCHI et al., 2010 Antibody recycling by engineered pH-dependent antigen binding improves the duration of antigen neutralization. Nat Biotechnol 28: 1203-1207.

IGAWA, T., A. MAEDA, K. HARAYA, T. TACHIBANA, Y. IWAYANAGI et al., 2013 Engineered monoclonal antibody with novel antigen-sweeping activity in vivo. PLoS One 8: e63236.

IIZUKA, A., C. NONOMURA, T. ASHIZAWA, R. KONDOU, K. OHSHIMA et al., 2019 A T-cell-engaging B7-H4/CD3-bispecific Fab-scFv Antibody Targets Human Breast Cancer. Clin Cancer Res 25: 2925-2934.

ITO, W., N. SAKATO, H. FUJIO, K. YUTANI, Y. ARATA et al., 1992 The His-probe method: effects of histidine residues introduced into the complementarity-determining regions of antibodies on antigen-antibody interactions at different pH values. FEBS Lett 309: 85-88.

KATO, Y., S. OZAWA, C. MIYAMOTO, Y. MAEHATA, A. SUZUKI et al., 2013 Acidic extracellular microenvironment and cancer. Cancer Cell Int 13: 89.

KJER-NIELSEN, L., M. A. DUNSTONE, L. KOSTENKO, L. K. ELY, T. BEDDOE et al., 2004 Crystal structure of the human T cell receptor CD3 epsilon gamma heterodimer complexed to the therapeutic mAb OKT3. Proc Natl Acad Sci USA 101: 7675-7680.

KOBOLD, S., S. PANTELYUSHIN, F. RATAJ and J. VOM BERG, 2018 Rationale for Combining Bispecific T Cell Activating Antibodies With Checkpoint Blockade for Cancer Therapy. Front Oncol 8: 285.

MURTAUGH, M. L., S. W. FANNING, T. M. SHARMA, A. M. TERRY and J. R. HORN, 2011 A combinatorial histidine scanning library approach to engineer highly pH-dependent protein switches. Protein Sci 20: 1619-1631.

ORR-WEAVER, T. L., J. W. SZOSTAK and R. J. ROTHSTEIN, 1983 Genetic applications of yeast transformation with linear and gapped plasmids. Methods Enzymol 101: 228-245.

PEGU, A., M. ASOKAN, L. WU, K. WANG, J. HATAYE et al., 2015 Activation and lysis of human CD4 cells latently infected with HIV-1. Nat Commun 6: 8447.

ROHANI, N., L. HAO, M. S. ALEXIS, B. A. JOUGHIN, K. KRISMER et al., 2019 Acidification of Tumor at Stromal Boundaries Drives Transcriptome Alterations Associated with Aggressive Phenotypes. Cancer Res 79: 1952-1966.

SARKAR, C. A., K. LOWENHAUPT, T. HORAN, T. C. BOONE, B. TIDOR et al., 2002 Rational cytokine design for increased lifetime and enhanced potency using pH-activated "histidine switching". Nat Biotechnol 20: 908-913.

SCHROTER, C., R. GUNTHER, L. RHIEL, S. BECKER, L. TOLEIKIS et al., 2015 A generic approach to engineer antibody pH-switches using combinatorial histidine scanning libraries and yeast display. MAbs 7: 138-151.

SHIPKOVA, M., and E. WIELAND, 2012 Surface markers of lymphocyte activation and markers of cell proliferation. Clin Chim Acta 413: 1338-1349.

SULEA, T., N. ROHANI, J. BAARDSNES, C. R. CORBEIL, C. DEPREZ et al., 2020 Structure-based engineering of pH-dependent antibody binding for selective targeting of solid-tumor microenvironment. MAbs 12: 1682866.

SUURS, F. V., M. N. LUB-DE HOOGE, E. G. E. DE VRIES and D. J. A. DE GROOT, 2019 A review of bispecific antibodies and antibody constructs in oncology and clinical challenges. Pharmacol Ther 201: 103-119.

WU, Z., and N. V. CHEUNG, 2018 T cell engaging bispecific antibody (T-BsAb): From technology to therapeutics. Pharmacol Ther 182: 161-175.

ZHANG, X., Y. LIN and R. J. GILLIES, 2010 Tumor pH and its measurement. J Nucl Med 51: 1167-1170.

Misc.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within the invention.

Where a sentence states that its subject is found in embodiments, or in certain embodiments, or in the like, it is applicable to any embodiment in which the subject matter can be logically applied.

This invention described herein is of antibodies that selectively bind CD3 in acidic conditions and methods of forming or using the same. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims. More specifically, those of skill will recognize that any embodiment described herein that those of skill would recognize could advantageously have a sub-feature of another embodiment, is described as having that sub-feature Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

Numbered Embodiments

The invention is further described with reference to the following numbered embodiments, which can be combined in each way implied by the language therein:

Antibody Embodiment 1. An isolated antibody that binds specifically to human CD3 in acidic conditions.

Antibody Embodiment 2. The isolated antibody of one of the Antibody Embodiments, which binds specifically to human CD3 in acidic conditions, but not significantly in neutral or physiological conditions.

Antibody Embodiment 3. The isolated antibody of one of the Antibody Embodiments comprising: light and heavy chain variable regions of anti-CD3-epsilon antibody or a variant thereof with the same or similar binding activity to human CD3, wherein at least one of the CDR domains of the light chain variable region is mutated by replacement of one or more amino acids within said CDR domains by a histidine residue and/or at least one of the CDR domains of the heavy chain variable region is mutated by replacement of one or more amino acids within said CDR domains by a histidine residue.

Antibody Embodiment 4. The isolated antibody or the antigen binding fragment thereof of one of the Antibody Embodiments, consisting of a CDR-H1, a CDR-H2 and a CDR-H3 that comprise an amino acid sequence of SEQ ID 1 for CDR-H1; of SEQ ID 2 or SEQ ID 3 for CDR-H2; and of SEQ ID 4 for CDR-H3 (TABLE 1).

Antibody Embodiment 5. The isolated antibody or the antigen binding fragment thereof of one of the Antibody Embodiments, consisting of a CDR-L1, a CDR-L2 and a CDR-L3 that comprise an amino acid sequence of SEQ ID 5 or SEQ ID 6 or SEQ ID 7 for CDR-L1; of SEQ ID 8 for CDR-L2; and of SEQ ID 9 or SEQ ID 10 for CDR-L3 (TABLE 2).

Antibody Embodiment 6. The isolated antibody or the antigen binding fragment thereof of one of the Antibody Embodiments, comprising a variable heavy chain amino acid sequence selected from the group consisting of SEQ ID 11; SEQ ID 12; SEQ ID 13; (TABLE 3).

Antibody Embodiment 7. The isolated antibody or the antigen binding fragment thereof of one of the Antibody Embodiments, comprising a variable light chain amino acid sequence selected from the group consisting of SEQ ID 14; SEQ ID 15; SEQ ID 16; or SEQ ID 17 (TABLE 4).

Antibody Embodiment 8. The isolated antibody or the antigen binding fragment thereof of one of the Antibody Embodiments, comprising: a variable heavy chain amino acid sequence selected from the group consisting of SEQ ID 12 and SEQ ID 13; and a variable light chain amino acid sequence selected from the group consisting SEQ ID 14; SEQ ID 15; SEQ ID 16; and SEQ ID 17.

Antibody Embodiment 9. (ABZ494) The isolated antibody or the antigen binding fragment thereof of one of the Antibody Embodiments wherein the mutated antibody or antigen binding fragment thereof bind specifically to human CD3 at acidic pH, but do not significantly bind to human CD3 at neutral or physiological pH comprising: the variable heavy chain amino acid sequence TABLE 5 (SEQ ID 12) and the variable light chain amino acid sequence TABLE 5 (SEQ ID 16)

Antibody Embodiment 10. (ABZ495) The isolated antibody or the antigen binding fragment thereof of one of the Antibody Embodiments; wherein the mutated antibody or antigen binding fragment thereof bind specifically to human CD3 at acidic pH, but do not significantly bind to human CD3 at neutral or physiological pH comprising: the variable heavy chain amino acid sequence TABLE 5 (SEQ ID 13) and the variable light chain amino acid sequence TABLE 5 (SEQ ID 15)

Antibody Embodiment 11. (ABZ497) The isolated antibody or the antigen binding fragment thereof of one of the Antibody Embodiments, wherein the mutated antibody or antigen binding fragment thereof bind specifically to human CD3 at acidic pH, but do not significantly bind to human CD3 at neutral or physiological pH comprising: the variable heavy chain amino acid sequence TABLE 5 (SEQ ID 12) and the variable light chain amino acid sequence TABLE 5 (SEQ ID 17)

Antibody Embodiment 12. The antibody or antigen binding fragment of one of the Antibody Embodiments, wherein the antibody or fragment thereof has the following characteristics: i. binds specifically to human CD3 at acidic pH, but does not significantly bind to human CD3 at neutral or physiological pH; ii. activates T cells at acidic pH while having significantly reduced activity at neutral or physiological pH Antibody Composition Embodiment 1. A pharmaceutical composition suitable for treatment of cancer disease, comprising: the isolated antibody or the antigen binding fragment thereof of one of the Antibody Embodiments, linked directly or indirectly to a cancer-interacting moiety—a chemical drug or biologic or recombinantly fused to a protein (e.g., a cancer-interacting protein or antibody to a cancer biomarker) to cross-link the host's T cells to cancer cells together with a pharmaceutically acceptable carrier, diluent or excipient and immune response modifier.

Antibody Production Embodiment 1. A method of producing an antibody or antigen binding fragment comprising: culturing a host cell comprising one or more polynucleotides encoding any one of the antibodies or antigen binding fragments of one of the Antibody Embodiments under conditions favorable to expression of the polynucleotide; and optionally, recovering the antibody or antigen binding fragment from the host cell and/or culture medium.

Antibody Treatment Embodiment 1. A method of treating cancer in a subject comprising administering to the subject an effective amount of the antibody or antigen binding fragment of one of the Antibody Embodiments, or of an expression vector which mediates expression of the antibody or antigen binding fragment within the subject, optionally in association with a further therapeutic agent or therapeutic procedure.

Antibody Treatment Embodiment 2. A method according to Antibody Treatment Embodiment 1, wherein the subject is a human.

Antibody Embodiment 21. An isolated antibody or antigen-binding fragment comprising light and heavy chain variable regions of anti-CD3-epsilon antibody, or a variant thereof with the same or similar binding activity to human CD3, but differing in that one or more of the following applies: (a) one or more of the CDR domains of the light chain variable region is mutated by replacement of one or more amino acids within said CDR domains by histidine residue(s) or (b) at least one of the CDR domains of the heavy chain variable region is mutated by replacement of one or more amino acids within said CDR domains by histidine residue(s), wherein the antibody or antigen-binding fragment binds CD3-epsilon (in a dimer or heterodimer such as with CD3-gamma, delta or zeta, particularly human CD3-epsilon) with greater affinity at pH 6.2 than at pH 7.4.

Antibody Embodiment 22. An isolated antibody or the antigen binding fragment thereof, wherein a variable heavy region retains 85% or more sequence identity with SEQ ID NO: 11 or 12 or 13 or the HCVR of SEQ ID NO: 25 or of BC-3, wherein a variable light region retains 85% sequence identity to SEQ ID NO: 14 or or 16, or 17 or the LCVR of SEQ ID NO: 25 or of BC-3, wherein within said variable sequences the CDRs retain 80% sequence identity as follows CDR-H1 to SEQ ID NO: 1; CDR-H2 to SEQ ID NO: 2 or 3; CDR-H3 to SEQ ID NO: 4; CDR-L1 to SEQ ID NO: 5 or 6 or 7; CDR-L2 to SEQ ID NO: 8; CDR-L3 to SEQ ID NO: 9 or 10; wherein the antibody binds CD3-epsilon at pH 6.2 with greater affinity than at pH 7.4, and wherein the antibody comprises one or more amino acid substitutions to histidine in one of said CDRs.

Antibody Embodiment 23. The isolated antibody or the antigen binding fragment thereof of an Antibody Embodiment, wherein the variable heavy region retains 90% or more sequence identity with SEQ ID NO: 11 or 12 or 13 or 23 or the HCVR of SEQ ID NO: 25 or of BC-3, and wherein the variable light region retains 90% sequence identity to SEQ ID NO: 14 or 15 or 16 or 17 or 24 or 27 or the LCVR of SEQ ID NO: 25 or of BC-3.

Antibody Embodiment 24. The isolated antibody or the antigen binding fragment thereof of an Antibody Embodiment, wherein the variable heavy region retains 95% or more sequence identity with SEQ ID NO: 11 or 12 or 13 or 23 or the HCVR of SEQ ID NO: 25 or of BC-3, and wherein the variable light region retains 95% sequence identity to SEQ ID NO: 14 or 15 or 16 or 17 or 24 or 27 or the LCVR of SEQ ID NO: 25 or of BC-3.

Antibody Embodiment 25. The isolated antibody or the antigen binding fragment thereof of an Antibody Embodiment, wherein the variable heavy region, outside the CDRs, retains 99% or more sequence identity with SEQ ID NO: 11 or 12 or 13 or 23 or the HCVR of SEQ ID NO: 25 or of BC-3, optionally 99.5% or 100%, and wherein the variable light region, outside the CDRs, retains 99% sequence identity to SEQ ID NO: 14 or 15 or 16 or 17 or 24 or 27 or the LCVR of SEQ ID NO: or of BC-3, optionally 99.5% or 100%.

Antibody Embodiment 26. The isolated antibody or the antigen binding fragment thereof of an Antibody Embodiment, wherein the histidine substitution is a Y, W, S, T or R to H substitution.

Antibody Embodiment 27. The isolated antibody or the antigen binding fragment thereof of an Antibody Embodiment, wherein the heavy chain has one or more histidine substitutions of SEQ ID NO: 3.

Antibody Embodiment 28. The isolated antibody or the antigen binding fragment thereof of an Antibody Embodiment, wherein one or more of the heavy chain CDRs has a sequence of SEQ ID NO: 3.

Antibody Embodiment 29. The isolated antibody or the antigen binding fragment thereof of an Antibody Embodiment, wherein the sixth to the eighth residue of CDR-H2 has a substitution to H.

Antibody Embodiment 30. The isolated antibody or the antigen binding fragment thereof of an Antibody Embodiment, wherein the seventh residue of CDR-H2 has a substitution to H.

Antibody Embodiment 31. The isolated antibody or the antigen binding fragment thereof of an Antibody Embodiment, wherein the light chain has one or more histidine substitutions of SEQ ID NO: 7.

Antibody Embodiment 32. The isolated antibody or the antigen binding fragment thereof of an Antibody Embodiment, wherein one or more of the light chain CDRs has a sequence of SEQ ID NO: 7.

Antibody Embodiment 33. The isolated antibody or the antigen binding fragment thereof of an Antibody Embodiment, wherein the sixth to the eighth residue of CDR-L1 has a substitution to H.

Antibody Embodiment 34. The isolated antibody or the antigen binding fragment thereof of an Antibody Embodiment, wherein the seventh residue of CDR-L1 has a substitution to H.

Antibody Embodiment 35. The isolated antibody or the antigen binding fragment thereof of an Antibody Embodiment, wherein the variable heavy chain sequence comprises SEQ ID NO: 11 or 12 or 13 or 23 or the HCVR of SEQ ID NO: or of BC-3.

Antibody Embodiment 36. The isolated antibody or the antigen binding fragment thereof of an Antibody Embodiment, wherein the variable heavy chain sequence comprises SEQ ID NO: 11 or 12 or 23 or the HCVR of SEQ ID NO: 25 or of BC-3 except that one to two residues are converted to H.

Antibody Embodiment 37. The isolated antibody or the antigen binding fragment thereof of an Antibody Embodiment, wherein the variable heavy chain sequence comprises SEQ ID NO: 11 or 12 or 23 or the HCVR of SEQ ID NO: 25 or of BC-3 except that one residue is converted to H.

Antibody Embodiment 38. The isolated antibody or the antigen binding fragment thereof of an Antibody Embodiment, wherein the variable heavy chain sequence comprises SEQ ID NO: 13.

Antibody Embodiment 39. The isolated antibody or the antigen binding fragment thereof of an Antibody Embodiment, wherein the variable light chain sequence comprises SEQ ID NO: 14, 15, 16 or 17 or 24 or 27 or the LCVR of SEQ ID NO: 25 or of BC-3.

Antibody Embodiment 40. The isolated antibody or the antigen binding fragment thereof of an Antibody Embodiment, wherein the variable light chain sequence comprises SEQ ID NO: 14 or 15 or 24 or 27 or the LCVR of SEQ ID NO: or of BC-3 except that one to two residues are converted to H.

Antibody Embodiment 41. The isolated antibody or the antigen binding fragment thereof of an Antibody Embodiment, wherein the variable light chain sequence comprises SEQ ID NO: 14 or 15 or 24 or 27 or the LCVR of SEQ ID NO: or of BC-3 except that one residue is converted to H.

Antibody Embodiment 42. The isolated antibody or the antigen binding fragment thereof of an Antibody Embodiment, wherein the variable light chain sequence comprises SEQ ID NO: 16 or 17.

Antibody Embodiment 43. The isolated antibody or the antigen binding fragment thereof of an Antibody Embodiment, wherein one of the following pairings applies: the variable heavy chain sequence comprises SEQ ID NO:12 and the variable light chain sequence comprises SEQ ID NO:16; the variable heavy chain sequence comprises SEQ ID NO:13 and the variable light chain sequence comprises SEQ ID NO:15; the variable heavy chain sequence comprises SEQ ID NO:12 and the variable light chain sequence comprises SEQ ID NO:17.

Antibody Embodiment 44. The isolated antibody or the antigen binding fragment thereof of an Antibody Embodiment, wherein the antibody or fragment thereof has one or more of the following characteristics: (i) binds specifically to human CD3-epsilon at pH 6.2 comparable to non-mutated OKT3, but 5-fold or more reduction in binding to human CD3 epsilon at pH 7.4 as measured by cytoflow analysis using yeast surface display; (ii) binds specifically to human CD3 receptor in human T cells at pH 6.2 comparable to non-mutated OKT3, but 3-fold or more reduction in binding to human CD3 receptor in human T cells at pH 7.4 as measured by human T cell cytoflow analysis; (iii) iii. activates T cells at pH 6.2 comparable to non-mutated OKT3 in the presence of CD28 agonist while having 2-fold or more reduced activity compared to non-mutated OKT3 at pH 7.4 as measured in a T-cell activation assay.

Antibody Embodiment 45. The isolated antibody or the antigen binding fragment thereof of an Antibody Embodiment, wherein the antibody or the antigen binding fragment is humanized.

Antibody Embodiment 46. The isolated antibody or the antigen binding fragment thereof of an Antibody Embodiment, wherein the sequence outside those sequences specified, has 95% or higher sequence identity with corresponding constant regions of known human or humanized antibodies of gene bank accession number ALJ79286, optionally, 98% or higher, or 99% or higher, or 99.5% or higher, or 100% identity.

Antibody Composition Embodiment 11. A pharmaceutical composition suitable for treatment of cancer disease, comprising: the isolated antibody or the antigen binding fragment thereof of an Antibody Embodiment, linked directly or indirectly to a moiety that interacts with a cancer cell [e.g., a chemical drug or biologic] such that the linked entities cross-link host's T cells to cancer cells, optionally together with a pharmaceutically acceptable carrier, diluent or excipient, optionally with an immune response modifier.

Antibody Production Embodiment 11. A method of producing an antibody or antigen binding fragment comprising: culturing a host cell comprising one or more polynucleotides encoding any one of the antibodies or antigen binding fragments of an Antibody Embodiment under conditions favorable to expression of the polynucleotide; and optionally, recovering the antibody or antigen binding fragment from the host cell and/or culture medium.

Antibody Treatment Embodiment 11. A method of treating cancer in a subject comprising administering to the subject an effective amount of the antibody or antigen binding fragment of an Antibody Embodiment, or of an expression vector which mediates expression of the antibody or antigen binding fragment within the subject, optionally in association with a further therapeutic agent or therapeutic procedure.

Antibody Treatment Embodiment 12. A method according to Antibody Treatment Embodiment 11, wherein the subject is a human.

What is claimed is:

1. An isolated antibody or antigen-binding fragment comprising light and heavy chain variable regions of an anti-CD3-epsilon antibody, or a variant thereof with binding activity to human CD3, comprising:
   CDR-H1 that comprises SEQ ID NO: 1;
   CDR-H3 that comprises SEQ ID NO: 4;
   CDR-L2 that comprises SEQ ID NO: 8; and
   CDR-L3 that comprises SEQ ID NO: 9 or SEQ ID NO: 10;
   wherein one or both of the following (1) or (2) applies:
     (1) CDR-H2 that comprises SEQ ID NO: 3; or
     (2) CDR-L1 that comprises SEQ ID NO: 7;
   wherein if (1) does not apply CDR-H2 comprises SEQ ID NO:2; and
   wherein if (2) does not apply CDR-L1 comprises SEQ ID NO: 5 or SEQ ID NO: 6;
   and
   wherein the antibody or antigen-binding fragment activates T cells at pH 6.2 comparable to non-mutated OKT3 in the presence of a CD28 agonist while having 2-fold or more reduced activity compared to non-mutated OKT3 at pH 7.4 as measured in a T-cell activation assay.

2. The isolated antibody or the antigen fragment thereof of claim 1, wherein either (1) and not (2) applies, or (2) and not (1) applies.

3. The isolated antibody or the antigen binding fragment thereof of claim 1, wherein (1) and not (2) applies.

4. The isolated antibody or the antigen binding fragment thereof of claim 1, wherein (2) and not (1) applies.

5. The isolated antibody or the antigen binding fragment thereof of claim 1, wherein the antibody or the antigen binding fragment is humanized.

6. A pharmaceutical composition suitable for treatment of cancer disease, comprising: the isolated antibody or the antigen binding fragment thereof of claim 1, linked directly or indirectly to a moiety that interacts with a cancer cell such that the linked entities cross-link host's T cells to cancer cells.

7. A method of producing an antibody or antigen binding fragment comprising: culturing a host cell comprising one or more polynucleotides encoding any one of the antibodies or antigen binding fragments of claim 1 under conditions favorable to expression of the polynucleotide.

8. A method of treating cancer in a human subject comprising administering to the subject an effective amount of the antibody or antigen binding fragment of claim 1, or of an expression vector which mediates expression of the antibody or antigen binding fragment within the subject.

9. A method according to claim 8, wherein the subject is a human.

10. An isolated antibody or the antigen binding fragment thereof comprising light and heavy chain variable regions of an anti-CD3-epsilon antibody, or a variant thereof with binding activity to human CD3, comprising: one of the following:
   a variable heavy chain sequence that comprises SEQ ID NO:12 and a variable light chain sequence that comprises SEQ ID NO:16;
   a variable heavy chain sequence that comprises SEQ ID NO:13 and a variable light chain sequence that comprises SEQ ID NO:15; or
   a variable heavy chain sequence that comprises SEQ ID NO:12 and a variable light chain sequence that comprises SEQ ID NO:17.

11. The isolated antibody or the antigen binding fragment thereof of claim 10, wherein the antibody or the antigen binding fragment is humanized.

12. A pharmaceutical composition suitable for treatment of cancer disease, comprising: the isolated antibody or the antigen binding fragment thereof of claim 10, linked directly or indirectly to a moiety that interacts with a cancer cell such that the linked entities cross-link host's T cells to cancer cells.

13. A method of producing an antibody or antigen binding fragment comprising: culturing a host cell comprising one or more polynucleotides encoding any one of the antibodies or antigen binding fragments of claim 10 under conditions favorable to expression of the polynucleotide.

14. A method of treating cancer in a subject comprising administering to the subject an effective amount of the antibody or antigen binding fragment of claim 10, or of an expression vector which mediates expression of the antibody or antigen binding fragment within the subject.

15. A method according to claim 14, wherein the subject is a human.

* * * * *